United States Patent [19]
Gamlyn et al.

[11] Patent Number: 5,749,367
[45] Date of Patent: May 12, 1998

[54] HEART MONITORING APPARATUS AND METHOD

[75] Inventors: Lee Gamlyn, Folkstone, United Kingdom; Siobhan O'Sullivan, Caheordavinlawn, Ireland; Philip Needham, Bracknell, United Kingdom; Tom Harris, Lightwater, United Kingdom

[73] Assignee: Cardionetics Limited, Hampshire, Great Britain

[21] Appl. No.: 709,539

[22] Filed: Sep. 5, 1996

[30]     Foreign Application Priority Data

Sep. 5, 1995 [GB] United Kingdom ............... 9518094

[51] Int. Cl.$^6$ ............................................. A61B 5/0452
[52] U.S. Cl. ............................................. 128/696
[58] Field of Search ........................... 128/696, 702, 128/699; 369/413.06

[56]             References Cited
              U.S. PATENT DOCUMENTS 3,832,994   9/1974   Bicher et al. .
5,280,792   1/1994   Leong et al. ............... 128/702

FOREIGN PATENT DOCUMENTS

0433626A2   6/1991   European Pat. Off. .
4307545A1   9/1994   Germany .
88/02237    4/1988   WIPO .

OTHER PUBLICATIONS

"Little waves, big squeeze", *New Scientist*, pp. 24–29, (Mar. 2, 1996).

Toni Conde, "Automatic Neural Detection of Anomalies In Electrocardiogram (ECG) Signals", *IEEE*, (Abstract), pp. 3552–3558, (1994).

Judith Dayhoff, "The Kohonen Feature Map", *Neutral Network Architectures*, pp. 163–191, (1990).

T. Harris, "'Neural–Maine': Intelligent On–Line Multiple Sensor Diagnostics For Complex Machinery", *Proceedings of the 8th International Congress on Condition Monitoring and Diagnostic Engineering Management* Queen's University Publication pp. 97–102, (1995).

Tom Harris, "An Introduction to neural networks", The International Journal for the Joining of Materials, pp. 4–6, (Mar. 1994).

Tom Harris, "High–Speed Tyre Test Monitoring Using Neural Networks", In Tire Technology International, UK and Int'l Press Ltd., 5 pages, (1994).

Tom Harris, "Neural Networks and their Application to Vibration Analysis", 17th Annual Energy–Sources Technology Conf., New Orleans, 3 pages, (Jan. 1994).

John MacIntyre, et al., "Neural Network Architectures and Their Application In Condition Monitoring", Proc. 6th Int'l. Conf. on COMDEM, Delhi, India, 8 pages, (Oct. 1994).

John MacIntyre, et al., "Neural Networks Applications In Condition Monitoring", Int'l. Conf. on App. of Artificial Intelligence in Engineering, Pennsylvania USA, 12 pages, (1994).

J. J. Soraghan, et al., "ECG Signal Compression using Classified Gain–Shape Vector Quantisation in the Wavelet Transform Domain", *Computers in Cardiology*, IEEE, pp. 373–376, (1995).

*Primary Examiner*—Scott Getzow
*Attorney, Agent, or Firm*—Schwegman, Lundberg, Woessner & Kluth, P.A.

[57]             ABSTRACT

A heart monitoring apparatus and method is disclosed wherein an electrocardiograph signal is obtained from a patient and processed to enhance the salient features and to suppress noise. A plurality n of values representative of the features of the electrocardiograph signal are generated and used in a Kohonen neural network to generate an n dimensional vector. This vector is compared with a stored plurality m of n dimensional reference vectors defining an n dimensional Kohonen feature map to determine the proximity of the vector to the reference vectors. If it is determined by the Kohonen neural network that the vector is within or beyond a threshold range of the reference vectors a signal is output which can be used to initiate an event such as the generation of an alarm or the storage of ECG data.

74 Claims, 24 Drawing Sheets

HEART MONITORING APPARATUS AND METHOD

The present invention generally relates to apparatus and a method for monitoring the operation of the heart of a patient. More specifically, the present invention relates to the analysis of electrocardiograph signals obtained from a patient using a neural network to monitor changes in the functioning or performance of the heart of a patient.

The electrical signals associated with muscular expansion and contraction of the heart and its chambers are frequently monitored to determine diseased conditions of the heart as well as deterioration and improvement of the condition of the heart, in particular following surgery or other treatment of the disease. The patients undergoing exercises or rehabilitation to improve the functioning of the heart.

Electrical signals of the heart are usually detected by means of conductive pads or contacts attached to the external chest wall and directly wired to a suitable machine which provides a graphical trace of the waveform, for a suitable display device on which the graphical wave form is represented for analysis by a suitably trained person. This however requires the patient to be permanently attached by wires to the monitoring apparatus and further requires the intervention of a suitably trained person.

Therefore an object of the present invention is to provide a heart monitoring apparatus and method which can monitor changes in heart condition automatically.

In accordance with one aspect the present invention provides heart monitoring apparatus comprising detection means for obtaining an electrocardiograph signal for a patient during a monitoring phase, preprocessing means for processing said electrocardiograph signal to enhance the salient features of the electrocardiograph signal and suppress the noise and to generate a plurality n of values representative of the features of said electrocardiograph signal, storage means for storing a plurality m of n dimensional reference vectors, Kohonen neural network means for receiving said plurality of values during the monitoring phase, for forming an end dimensional vector from said plurality of values, and for comparing said n dimensional vectors with said stored plurality m of n dimensional reference vectors defining an n dimension Kohonen feature map to determine the proximity of said n dimensional vector to said reference vectors, and output means for outputting a signal if said Kohonen neural network means determines that said n dimensional vector is within or beyond a threshold range of said reference vectors.

In accordance with a second aspect of the present invention there is provided a heart monitoring method comprising the steps of obtaining an electrocardiograph signal from a patient during a monitoring phase, preprocessing the electrocardiograph signal to enhance the salient features of the electrocardiograph signal and suppress the noise, and to generate a plurality of n of values representative of the features of the electrocardiograph signal, forming an n dimensional vector from the plurality of values, comparing the n dimensional vector with a stored plurality m of n dimensional reference vectors defining an n dimensional Kohonen feature map to determine the proximity of the n dimension vector to said reference vectors, and outputting a signal if it is determined that the n dimensional vector is within or beyond a threshold range of said reference vectors.

In order for the Kohonen neural network means to generate the n dimensional Kohonen feature map, in accordance with one embodiment, during a learning phase, a plurality of reference values are input to the Kohonen neural network, which values are representative of features of a reference electrocardiograph signal. The Kohonen neural network generates the n dimensional Kohonen feature map having the plurality m of reference vectors and these reference vectors are stored in the storage means.

The reference electrocardiograph signal can either be obtained from the patient during the learning phase to provide patient specific normal data, or the reference electrocardiograph signal can be obtained from a large sample of the population to represent general normal heart operation. In either case the Kohonen neural network means operates during the monitoring phase to determine whether the n dimensional vector or the electrocardiograph signal lies outside a predetermined range of the reference vectors. If it is determined that the n dimensional vector lies outside the predetermined range an output signal is generated. This output signal can be used to trigger an event such as the generation of a warning, or the triggering of storage of the electrocardiograph signal either in an unprocessed condition or as the plurality of values. Also, the electrocardiograph signal could be stored in a compressed form other than as the plurality of values. Further, the output signal which can comprise an error vector can be used for further processing in order, for example to monitor the level of stress experienced by the heart.

In an alternative embodiment, the learning phase can be omitted and the plurality m of n dimensional reference vectors defining the n dimension Kohonen feature map can be input directly where these have been learnt previously on for instance another machine.

In another embodiment of the present invention which can be used for detecting specific heart conditions, at least one set of reference vectors can be built into the Kohonen feature map either by directly inputting the vectors or by learning them from one or more sets of electrocardiograph signals representing known abnormalities. In this way, during the monitoring phase, when it is detecting by the Kohonen neural network means that the n dimensional vector lies inside a predetermined range of the abnormal reference vectors, an output signal can be generated which can be used to trigger an alarm and/or trigger the storage of the electrocardiograph signal.

In one embodiment of the present invention the Kohonen neural network means is adapted to carry out the comparison and determination by determining the differences between the reference vectors and the plurality of values for each dimension, summing the individual dimensional differences, and comparing the sum with a threshold difference value.

In an alternative embodiment of the present invention the Kohonen neural network means is adapted to carry out the comparison and determination by mapping the plurality of values onto the Kohonen feature map, calculating the differences therebetween by Pythagoras law, and comparing the differences with at least one difference threshold.

Therefore, in accordance with either of these embodiments it is determined that the threshold has been exceeded, an output signal can be generated. This signal could simply be a trigger signal or can comprise the error vector between the n dimensional vector and the nearest reference vector in the n dimensional Kohonen feature map. If the error vector is output, this can be used for further processing together with other heart operation related signals in order to measure the level of stress experienced by the heart.

In one embodiment the further processing is carried out by a neural network such as the multi-layer perceptron. The other signals which can be input are for example the heart rate, the heart rate variability, and other specific features related to the shape of the electrocardiograph signal.

In order to condition the electrocardiograph signals for input to the Kohonen neural network, they are pre-processed in order to provide n values to form the n dimensional vector.

In one embodiment the n values are obtained by extracting n important features of the electrocardiograph signal e.g. by selecting peaks and other specific features.

In an alternative embodiment of the present invention the electrocardiograph signal is transformed using a Fourier transform and/or a Wavelett transform.

Because an electrocardiograph trace can include distinctive irregular heartbeats such as an ectopic beat, one embodiment of the present invention includes means to remove the distinctive irregular heartbeats from the electrocardiograph signal which is processed by the Kohonen neural network to generate the output signal.

Since such irregular heartbeats can include distinctive frequency components e.g. a ventricular ectopic beat comprises a significant low frequency component, a high pass filter can be used to remove such beats and a low pass filter can be used to identify and indicate when such beats occur.

In an alternative embodiment of the present invention the Kohonen neural network uses two different sets of reference vectors and operates in two steps to initially separate the distinctive irregular beats. A first set of n dimensional reference vectors are stored for identification of the distinctive irregular beats and a second set of n dimensional reference vectors are stored for monitoring regular heartbeats. During the monitoring phase the Kohonen neural network operates to initially compare the n dimensional vector with the stored first set of reference vectors to identify the distinctive irregular heartbeats, and to subsequently compare an n dimensional vector formed from regular heartbeats excluding the distinctive irregular heartbeats with the second set of n dimensional reference vectors. Thus in accordance with this method the Kohonen neural network can identify a distinctive irregular heartbeat by determining if the n dimensional vector falls within a threshold range of the first set of reference vectors. The identified distinctive irregular heartbeats can then be ignored in the subsequent step carried out by the Kohonen network means and a count can be kept of their occurrence.

In addition to the removal of distinctive irregular heartbeats from the electrocardiograph signal, in order to increase the signal to noise ratio, the electrocardiograph signal or the plurality of values are preferably averaged over several regular heartbeats. Also, to increase accuracy the average values are preferably normalised by reducing the values and dividing by the standard deviation.

In this way the electrocardiograph signals are preprocessed to remove distinctive irregular beats and to significantly improve the signal to noise ratio thereby reducing the number of false identifications of novel electrocardiograph signals by the Kohonen neural network. The present invention can thus provide a heart monitoring apparatus which can monitor changes in heart operation during the monitoring phase. The apparatus can be set to operate using either patient specific normal data or normal data representative of the population. Also, the apparatus can be sensitive to detect specific heart conditions which are represented by a specific and distinctive electrocardiograph shape.

When the apparatus is used with patient's specific normal data, the normal range for heart operation can simply be learnt during the learning phase such as whilst a patient is still in hospital or still in intensive care. Subsequently the functioning of the heart can be compared with the normal patient specific range during a monitoring phase e.g. following discharge from the hospital or following a period of observation on a ward away from intensive care. In this patient specific mode, if the functioning of the heart is determined by the Kohonen neural network as straying from within the normal range learnt during the normal phase, then an event can be triggered such as the raising of an alarm or the storage of electrocardiograph data. The raising of the alarm can allow for the intervention of a suitably trained person. Whilst the alarm can indicate a deterioration in the condition of the patient, it can equally indicate an improvement in the condition of the patient. Thus, in this patient specific mode, in either case, if the normal range of operation of the patient's heart has moved, the apparatus can be set into its learning phase once more to relearn the patient's normal heart operation range.

An important aspect in the present invention is that in the present invention a change in functioning of the heart is determined by considering a full analysis of the electrocardiograph signal rather than by merely taking into consideration the pulse rate. In the present invention the Kohonen neural network is able to analysis the shape of the electrocardiograph signal.

The advantage of having training data derived from the sample of the population is that some of the information contained within the electrocardiograph signal is common across all patients. In addition, by having training data derived from the patient, the individual's unique features may also be classified. By obtaining both types of data the classification of electrocardiograph patterns is possible.

An embodiment of the present invention can comprise a self-contained battery operated portable unit incorporating a display and/or an audio output to indicate the presence of an alarm and/or the level of stress. Also, a connector for the transfer of classified or stored data can be provided to allow the display or printing of data for a subsequent analysis by a suitably trained person. The present invention can also be embodied as a remote monitoring arrangement wherein the detection means and the output means are remote from one another and communicate with one another by airborne communication e.g. radio frequency signals. This provides the advantage that the patient is not restricted by wires normally provided for an electrocardiograph apparatus and this arrangement is therefore ideally suited for a wide range of applications.

The remote monitoring embodiment of the present invention may take many forms. The electrocardiograph signals can be transmitted in either an analogue or digital form or indeed the module which is attached to the patient could carry out the processing and even some form of limited display and/or alarm. In one embodiment, only an output signal could be transmitted to a remote station.

Embodiments of the present invention will now be described with reference to the accompanying drawings, in which.

Figure 1:
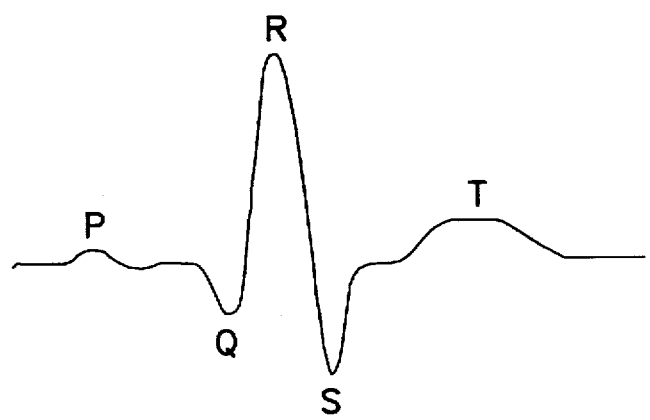
FIG. 1 is an example of an electrocardiograph trace.

Referring now to the drawings, FIG. 1 illustrates a typical electrocardiograph trace wherein various features P, Q, R, S and T can be seen. The shape and size of each of the features is an important indication of the condition and operation of the heart. The shape of the electrocardiograph trace for any two patients is never exactly the same and therefore detecting differences and specific heart conditions for patients requires significant skill by a medical practitioner. The present invention is directed towards obtaining information on the shape of the electrocardiograph trace to enable an automatic detection of a change.

Figure 2:
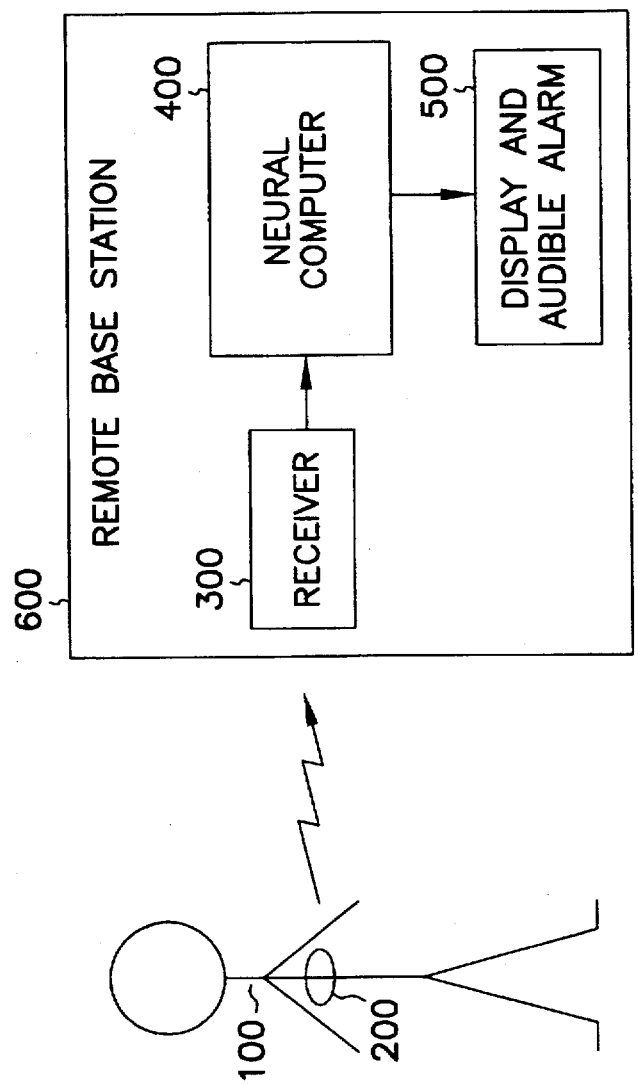
FIG. 2 is a schematic diagram of the heart monitoring apparatus in accordance with one embodiment of the present invention.

FIG. 2 illustrates a highly schematic remote heart monitoring apparatus in accordance with one embodiment of the present invention. A patient 100 is fitted with a portable housing 200 which can obtain an electrocardiograph signal from the patient 100 and transmit this to the remote base station 600. The electrocardiograph signal can be obtained from the patient using conventional electrodes such as an arrangement of three electrodes in line with existing medical practices. Two of the electrodes can detect a differential signal whilst the third can provide a common or reference signal. The differentially detecting signal can then be transmitted to the remote base station 600 for analysis. As will be seen hereinafter in accordance with another embodiment of the present invention, the analysis of the electrocardiograph signal can also take place within the portable housing 200 carried by the patient.

Conveniently, the portable housing 200 can be carried by the patient 100 by placing it within a pocket in a vest or similar garment so that the electrodes are held against the patient's skin at the correct position. Alternatively, the electrodes are provided separate from the housing and connected thereto by wires. At the remote base station 600 the transmitted electrocardiograph signal is received by a receiver 300 and passed to a neural computer 400 to processing. The neural computer 400 analyses the electrocardiograph signal and passes the signal to a display and audible alarm device 500 if a novel electrocardiograph signal is detected. A neural computer is also capable of storing the electrocardiograph signal for the conventional analysis by a skilled medical practitioner.

Figure 3:
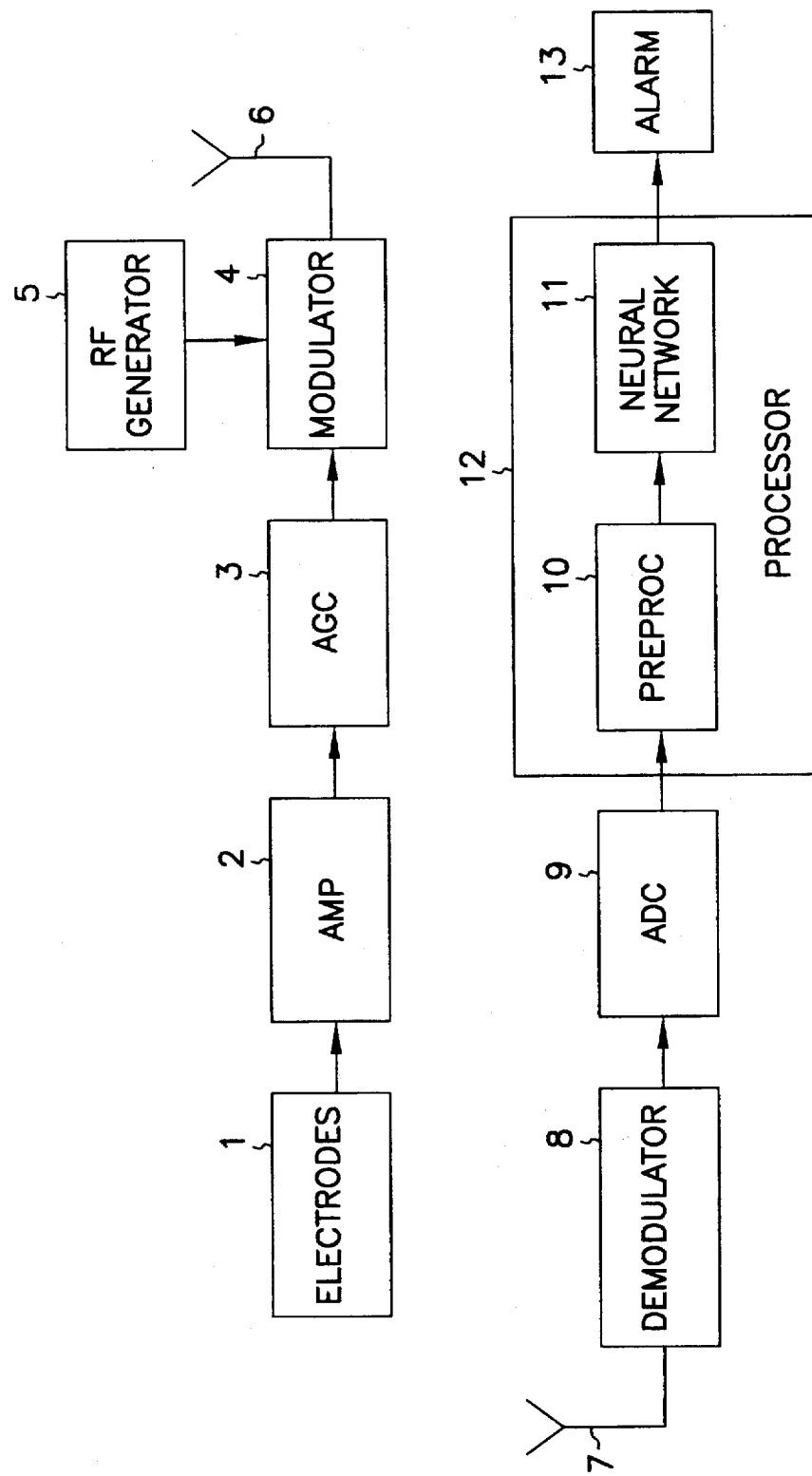
FIG. 3 is a more detailed schematic diagram of the apparatus in accordance with one embodiment of the present invention.

FIG. 3 illustrates in more detail one embodiment of the present invention wherein the electrocardiograph signal is transmitted as a radio frequency signal. The electrocardiograph signal detected by the electrodes 1 is passed to an instrument amplifier 2 having characteristics of very high input impedance, very low common mode signal rejection and forward gain of 1000 over a bandwidth of 0.01 Hz to 500 Hz. The output of the amplifier 2 is then fed to a very slow response automatic gain control circuit 3 to ensure that the peak output signal level is kept reasonably constant at the maximum permitted modulation level without introducing distortion. The signal is then modulated in a modulated form with an RF signal generated by the RF generator 5. AM or FM modulation may be used as appropriate. The signal is then passed to an antenna 6 for transmission. The radio transmitter is a low power short range circuit designed for operation within a building or hospital ward, and with a frequency stability such that multiple channels may operate within the frequency band. At the base station, a radio receiver comprising an antenna 7 and a demodulator 8 receive and demodulate the cardiac signal, one per channel, each sensitive enough to detect the low power transmitted signal and selective enough to discriminate between adjacent signals without interference. The cardiac signal is then converted to a digital signal by means of a linear analogue to digital converter 9 at a sampling rate of 500 Hz, and resolving its sample of the analogue signal into a binary number between and twelve and sixteen bits in length. The binary code signal is then passed to the processor 12 for pre-processing within the pre-processor unit 10. The preprocessor signals are then passed to the neural network 11 for analysis and if a normal electrocardiograph trace is determined an output is triggered which in the current example causes an alarm unit 13 to raise an audible and/or visual alarm. In addition or instead, the output can trigger storage and possibly the display of the electrocardiograph trace.

Figure 4:
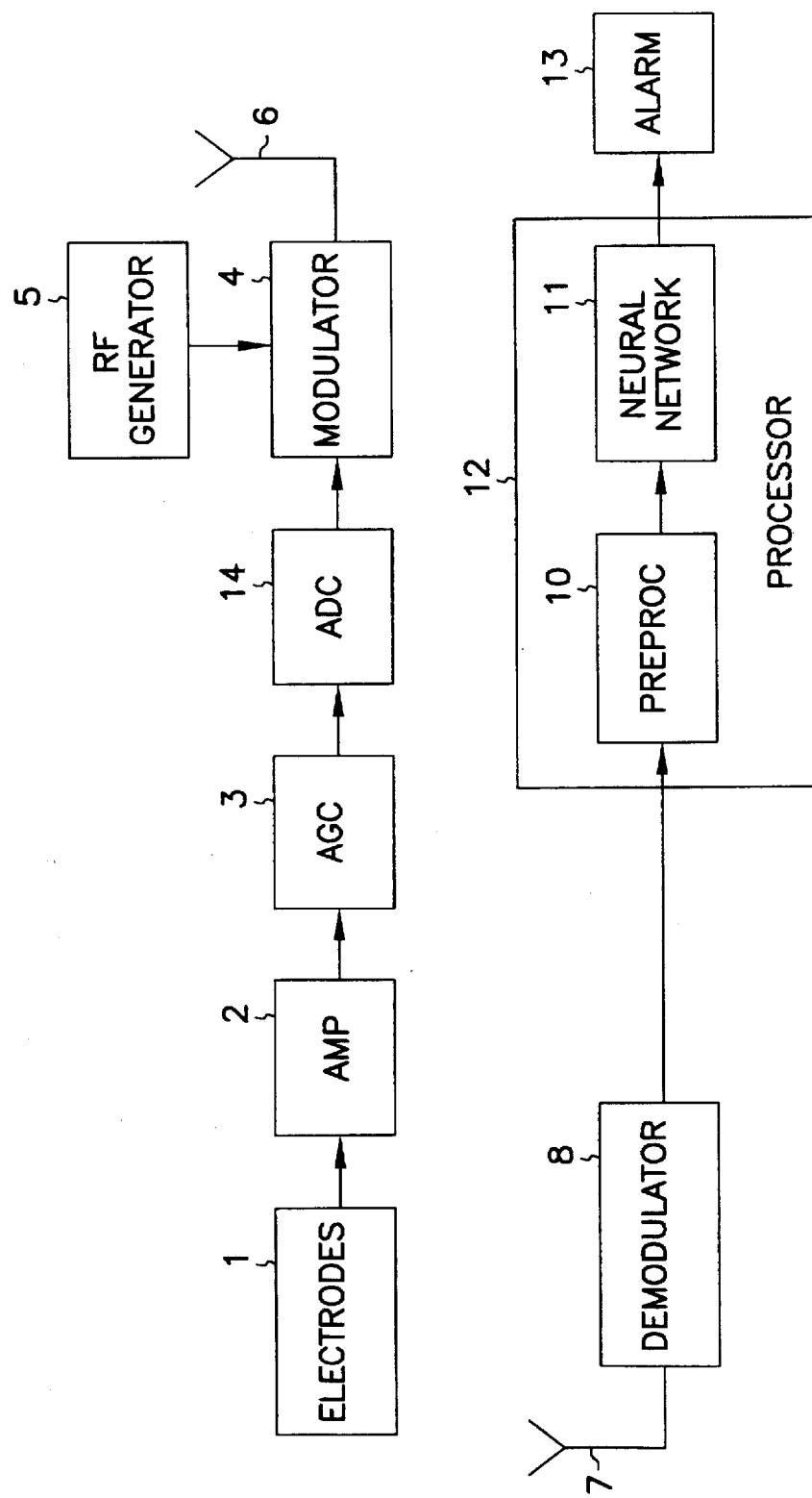
FIG. 4 is a more detailed schematic diagram of the apparatus in accordance with a second embodiment of the present invention.

FIG. 4 illustrates a second embodiment of the present invention wherein an electrocardiograph signal detected by the electrodes 1 is passed to an instrumentation amplifier 2 and automatic gain control circuit 3 as for the previous embodiment. However, before onward transmission to the radio transmitter, the signal is digitised by an analogue to digital converter 14 to form a binary bit stream which is then used to modulate the RF signal from the RF generator 5 in the modulator 4.

At the base station, the receiver comprises the antenna 7 and the demodulator 8 demodulates the received signal to provide a digital signal which is a digitised sample of the original analogue signal. This signal is then passed into the processor 12 and is analyzed in the same manner as for the previous embodiment.

Figure 5:
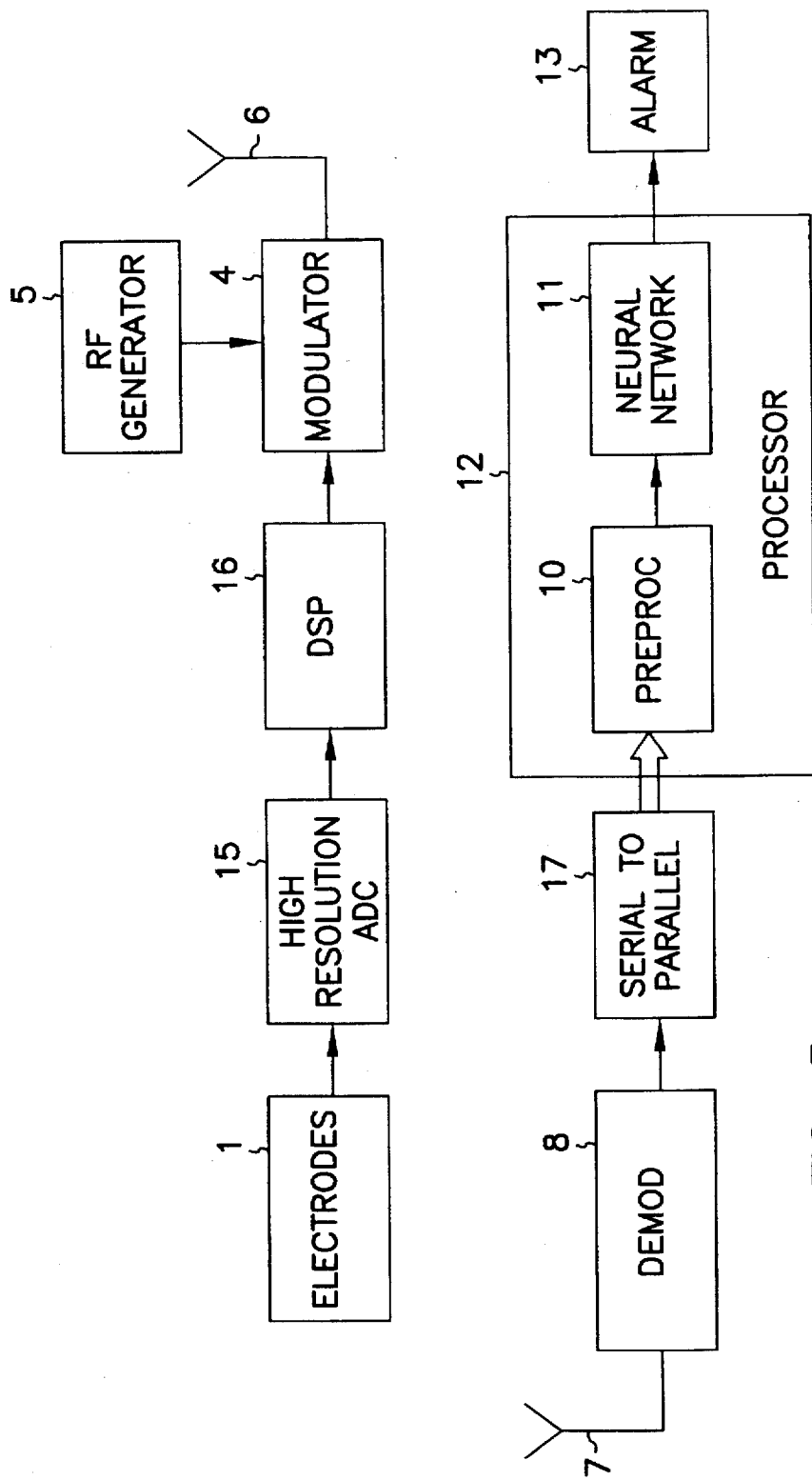
FIG. 5 is a more detailed schematic diagram of the apparatus in accordance with a third embodiment of the present invention.

Referring now to FIG. 5 there is illustrated a third embodiment of the present invention wherein the electrocardiograph signal from the electrodes is directly processed by a high resolution analogue digital converter 15 capable of resolving to better than one micro-volt. The digitised signal is then processed using a digital signal processor 16 to normalise the amplitude, improve the signal to noise level and bandwidth limit the signal. The digital data from the digital signal processor 16 is then used to modulate an RF signal from the RF generator 5 using the modulator 4.

At the base station the RF signal is demodulated and the serial digital signal is then converted to the parallel in unit 17. The parallel signal comprises twelve to sixteen bit binary coded words which are presented to the processor 12 at a rate of 500 Hz. The processor 12 then operates on the received signal in the same manner as for the previous embodiments.

Figure 6:
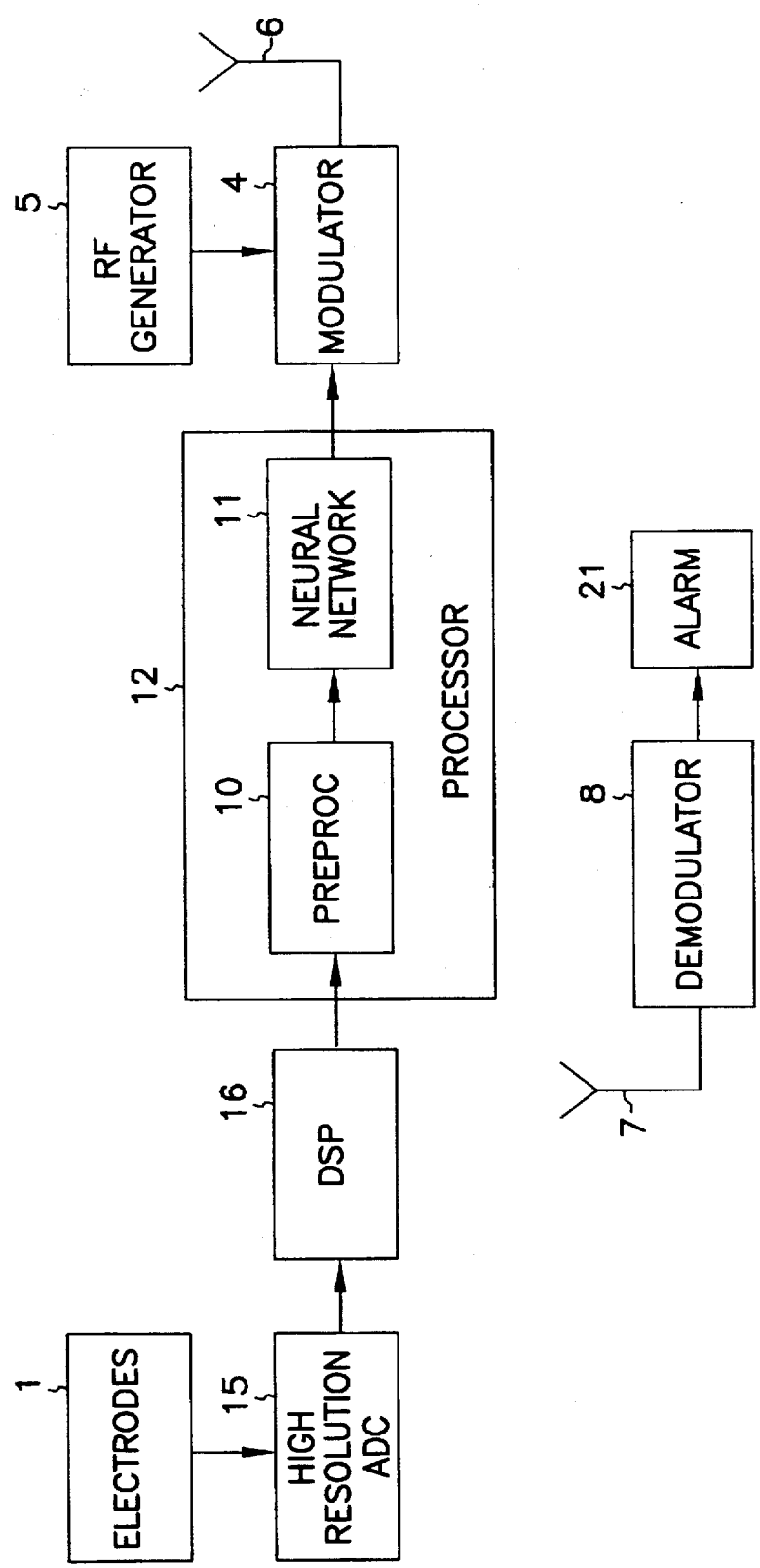
FIG. 6 is a more detailed schematic diagram of the apparatus in accordance with a fourth embodiment of the present invention.

FIG. 6 illustrates a fourth embodiment of the present invention which is similar to the previous embodiment of the present invention except that the analysis of the electrocardiograph signal takes place within the portable housing carried by the patient. The electrocardiograph signal from the electrodes 1 is passed to a high resolution analogue to digital converter 15. The output of the high resolution analogue to digital converter 15 is then passed to a digital signal processor 16 to normalise the amplitude, improve the signal to noise level and bandwidth limit the signal. The output of the digital signal processor 16 is then passed to the processor 12 wherein the electrocardiograph signal is first pre-processed in the pre-processing unit 10. The pre-processed data is then passed to the neural network 11 for analysis. If a novel electrocardiograph trace is determined, an output signal is generated which is in the present embodiment an alarm signal. This signal is then passed to the modulator 4 for modulating the RF signal from the RF generator 5. The modulated RF signal is then transmitted by the antenna 6. At the base station, the antenna 7 receives the modulated RF signal which is then demodulated in the demodulator 8. The alarm signal is then passed to an alarm unit 21 to generate an audible or visual alarm.

In addition to the alarm unit, the neural network 11 can output summary data of the cardiac signal such as heart rate. The alarm unit 21 can also receive such summary data for display.

Figure 7:
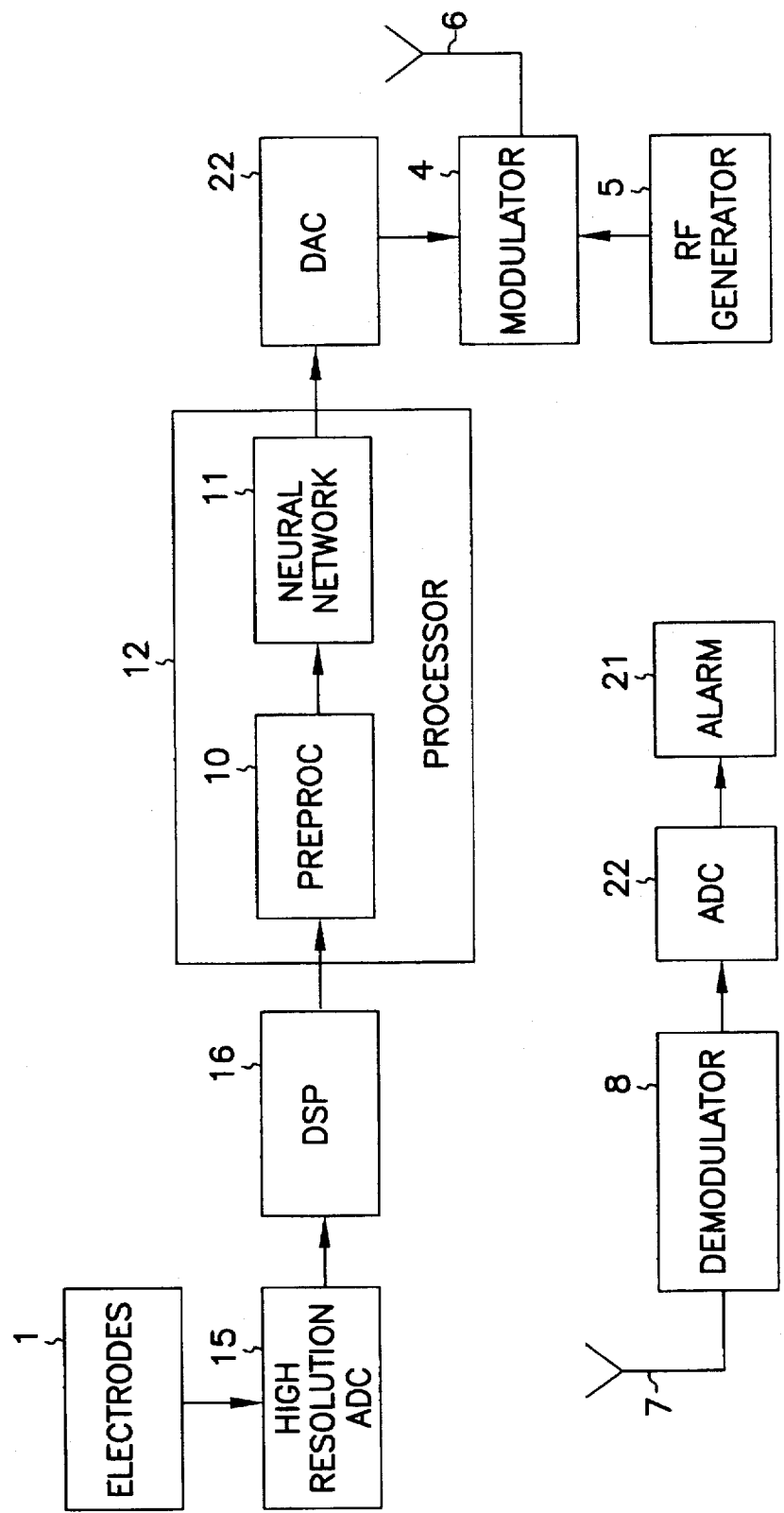
FIG. 7 is a more detailed schematic diagram of the apparatus in accordance with a fifth embodiment of the present invention.

FIG. 7 illustrates a fifth embodiment of the present invention which is similar to the embodiment of FIG. 6 except that the signals are transmitted in analogue form. The output of the neural network 11 is passed to a digital to analogue converter 22. The analogue output of the digital to analogue converter 22 is then used for modulation of the RF signal from the RF generator 5 in the modulator 4.

At the base station the analogue output of the demodulator 8 is digitised using an analogue to digital converter 22 and the digital signal is then passed to the alarm unit 21. In embodiments 1 to 5 described hereinabove the raw electrocardiograph signal itself is not suitable for immediate processing by the neural computer. Small variations in the signal are significant and need to be detected, but when embedded in the whole signal they become numerically insignificant compared with the noise level, thus making it virtually impossible to carry out novelty detection on the raw signal. To overcome this, digital signal processing techniques are used to extract information from the received signal. Extracted information comprises significant features in the electrocardiograph signal which are measured and used by the neural computer to detect novelty.

The features that are important in an electrocardiograph signal are peak heights and the separation between peaks. One method of pre-processing the electrocardiograph signal is to utilize the fast Fourier transform (FFT). The fast Fourier transform obtains frequency information. Another or complementary technique is to use the Wavelett transform. Alternatively, as will be described hereinafter with reference to the sixth embodiment, features can be extracted from the electrocardiograph signal.

In one embodiment the electrocardiograph signal is sampled at the frequency of 50 Hz typically a sample of 4 seconds is used which will typically provide at least five complete heartbeat signals within the window. Preparing this data for the fast Fourier transform (FFT) can take a number of forms.

1. First 128 samples can be presented to a standard FFT algorithm to obtain 64 real and 64 imaginary components.

2. A peak search can be carried out in the first quarter of the data to find the highest amplitude signal. This can be assumed to be a capital R point on the electrocardiograph. The following 128 samples can be presented to a standard FFT algorithm to obtain 64 and 64 imaginary components. This has the advantage of synchronising the data and resulting in a less noisy FFT.

3. The peak search can be carried out in the second quarter of the data to find the highest amplitude sample. This can be assumed to be an R point on the electrocardiograph. 128 samples can be selected from a fixed number of samples preceding the peak. These samples can then be presented to the standard FFT algorithm to obtain 64 real and 64 imaginary components. This has the advantage over the second method given above of reducing the edge effect caused by starting the sample with a peak.

Any of the above methods can be enhanced with the use of apodisation, i.e. an edge effect reducing algorithm such as a hanning window.

More than one pulse is included in the sample presented to the FFT to allow pulse rate information to be taken into account. An alternative embodiment can use a single electrocardiograph pulse for pre-processing and a separate pulse rate algorithm to calculate the pulse rate. This may make the FFT more sensitive to subtle changes in the electrocardiograph waveform.

Preferably only the real components of the fast Fourier transform are used in the Kohonen feature map. However, the imaginary components or a power spectrum can also be used instead of or in addition to the real components.

Figure 8:
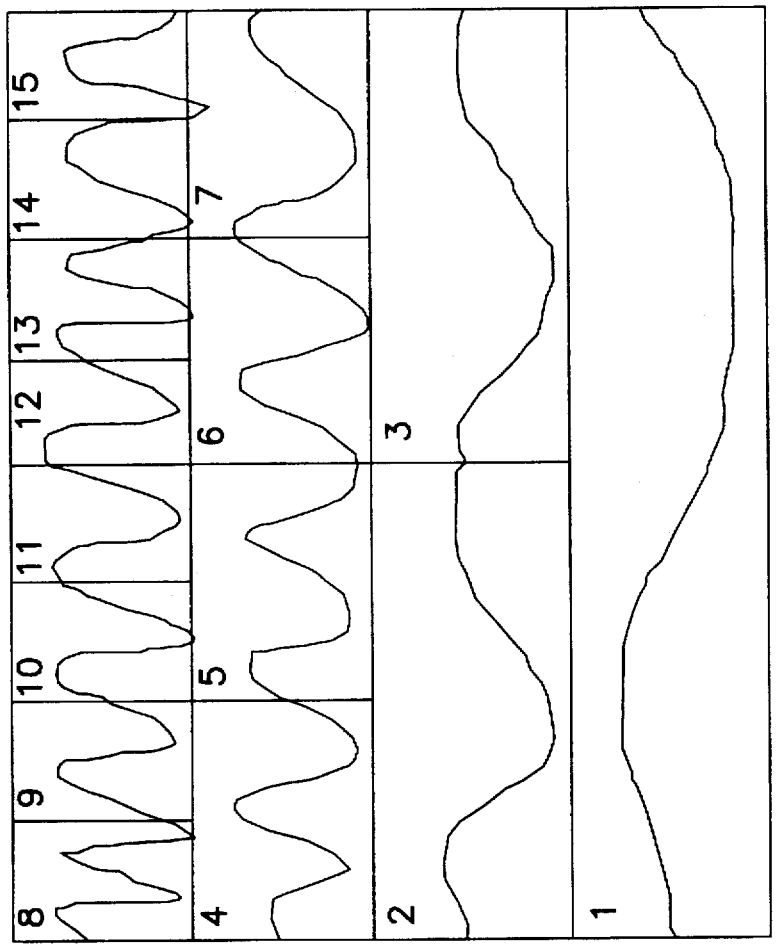
FIG. 8 is a diagram illustrating the principles of wavelet transformation.

In addition to, or instead of, the fast Fourier transform, Wavelett transforms can be used to pre-process the raw electrocardiograph signal. This transform operates by measuring the similarity of the signal to a set of defined wave functions. Such a set of wave functions are illustrated in FIG. 8. The wave functions are arranged in a hierarchy so that output is scaler in nature. The transform can provide typically 64 values.

As with the fast Fourier transform, multiple pulses could be presented or a single pulse with additional pulse rate information given separately. The Wavelett transform method also requires that the signal is synchronised.

In one embodiment all of the values produced by the fast Fourier transform and the Wavelett transform are used as inputs to the Kohonen feature map. A system using the fast Fourier transform with a multiple pulse window provides 64 values which are the real components of the fast Fourier transform and which forms a vector having 64 values for the Kohonen feature map. Where both the fast Fourier transform and the Wavelett transform are used for a single pulse window, 128 values, comprising 64 fast Fourier transform values and 64 Wavelett transform values are provided.

The neural computer operates as a Kohonen feature map. Such a neural network is well known and reference to this can be found in 'Neural Network Architectures. An introduction', J Dayhoff, Van Nostrand, Reinhold 1990, pages 163 to 191.

Feature mapping in the Kohonen feature map is a process by which example training vectors are clustered in featured space. The pre-processed values from an electrocardiograph signal define a vector position in an Euclidean multi-dimensional space. The dimensionality of the space is determined by the number of features measured i.e. the number of values. For example if two features are measured with values of 5 and 3 the vector position for that electrocardiograph is (5, 3) in a two dimensional space. In the embodiments of the present invention described hereinabove, where 64 FFT values are provided, the feature space is a 64 dimensional space. For a more complex embodiment using the fast Fourier transform output and the Wavelett transform output the Kohonen feature map has 128 dimensions.

Figure 9A:
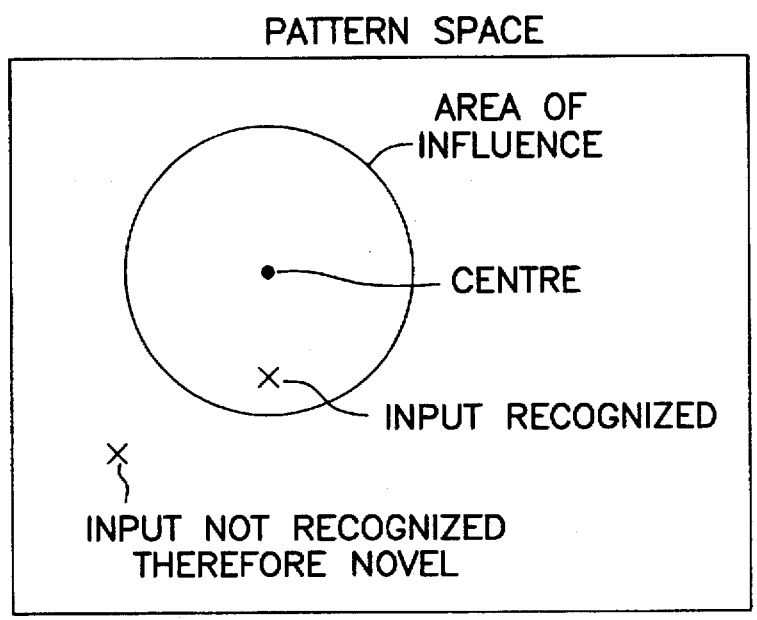
FIG. 9A is a diagram of a two dimensional pattern space illustrating novelty detection.
Figure 9B:
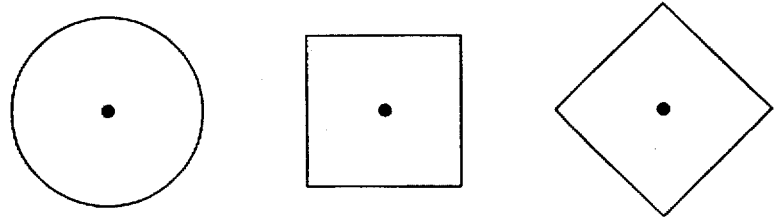
FIG. 9B illustrates alternative shapes from the regions around the reference vectors.

In the Kohonen feature map a plurality of reference vectors are used which are initially randomly positioned in the multi-dimensional space. During a learning phase when values are input to the Kohonen feature map, the position of the reference vectors are moved to represent the distribution of the values in the feature space. Each of the reference vectors has a point in the multi-dimensional space which is its centre and can have a predefined area of influence therearound. This is illustrated in FIG. 9A. The area surrounding the reference vector defines a predetermined distance in pattern space from the reference vector. As can be seen in FIG. 9B, the shape of the area of influence can be varied between radial, square and diamond, respectively. The radial area of influence is the most accurate but is the most complex to compute.

FIG. 9A illustrates a single reference vector is a two dimensional space. Surrounding the reference vector is the predetermined region which is considered to be within the range of the reference vector. If the reference vector were to represent a learnt reference vector or an electrocardiograph signal, when an electrocardiograph value is input in the monitoring phase, if it falls within the area of influence it is recognised whereas if it falls outside the area of influence it is not recognised and there is therefore considered to be novelty: resulting in the generation of an output signal which can for instance trigger an alarm or trigger the storage of the electrocardiograph signal. Also, the error vector which is the vector between the nearest reference vector and the vector of the input data can be output.

Considering for simplicity the two dimensional pattern of space, if a reference vector has a position (5, 3) and the electrocardiograph signal obtained during a measuring phase has a vector position of (6, 2.5), the difference between the two can be calculated either by pythagoras' law or simply by summing individual dimensional differences: which in this case gives the difference of 1.5.

Feature mapping defines reference positions in the feature space which describe "normal" positions for an electrocardiograph signal. A threshold can be set around each reference vector which describes the limit of the vectors represented in space. Thus the difference of, for example, 2.2 can be defined as no longer represented by the "normal" vector and there is thus novelty. This is illustrated in FIG. 9A.

The position of the reference vectors is determined during a training process which is described in more detail in the book by J Dayhoff. The algorithm takes the form of a neural network which each neuron network defines a reference vector position. Given the sample data, an iterative learning process is used to find the optimum position for all of the reference vectors based on the position and density of the example data. This is the networks training process.

Figure 10:
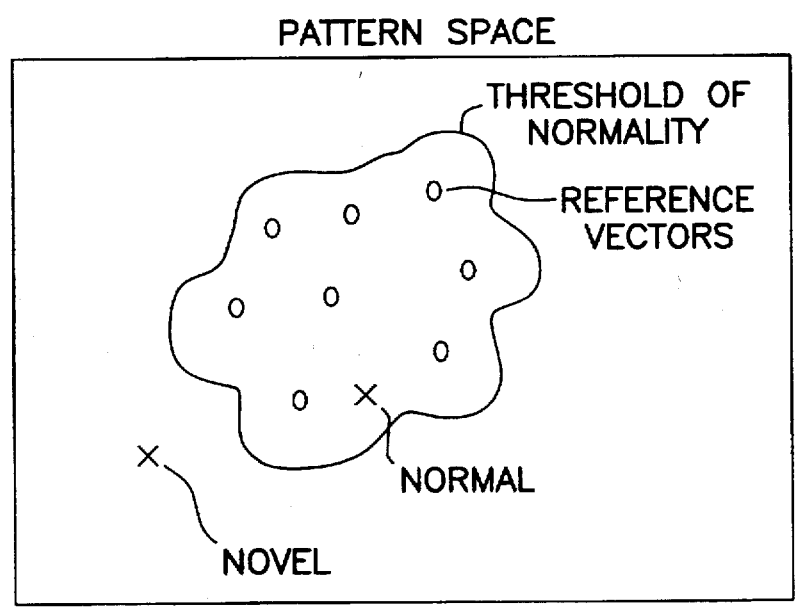
FIG. 10 is a diagram of a two dimensional pattern space illustrating the principles of novelty detection.

FIG. 10 illustrates a simple case of a two dimensional pattern space having eight reference vectors, each with their own area of influence. The reference values represent optimised mean values derived from the electrocardiograph values during the learning phase and are placed according to the distribution and density within the pattern space. The periphery of the area of influence for each of the reference vectors therefore defines a threshold of normality for the electrocardiograph signal based on the electrocardiograph signals during the learning phase.

FIG. 10 illustrates two electrocardiograph values for this two dimensional hypothetical example: one representing a normal electrocardiograph signal which falls within the threshold of normality and one representing a novel electrocardiograph signal which falls outside the threshold of normality.

In one embodiment of the present invention where for example a patient is being monitored in a hospital environment, example data is collected from the patient used to train the network. In an alternative embodiment training data can be obtained from electrocardiograph signals from a large sample of the population. A set of reference vectors will be defined and the reference vectors collected from the patient will be unique to that patient. During the monitoring phase the pre-processed electrocardiograph values are input to the neural computer to determine the difference between the reference vectors either by using Pythagoras' law or simply by summing the individual dimension differences. Alternatively, a radial basis function algorithm can be used. In this case the centres and widths of the functions are defined by a similar training process as above. Each centre has a region of influence which may be radial, square or binary shaped, as shown in FIGS. 9A and 9B. When an input is presented to the patent space if it falls inside at least one centre region it is recognised, otherwise it is treated as a novelty.

Figure 11:
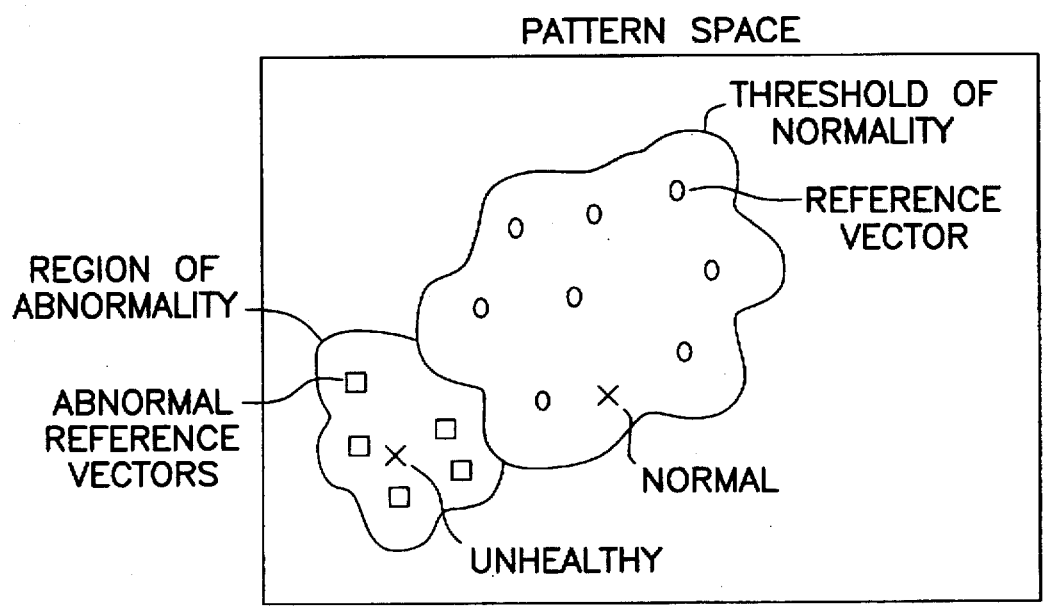
FIG. 11 is a diagram of a two dimensional pattern space illustrating the principles of both novelty detection and the diagnosis of a specific heart condition.

FIG. 11 illustrates a further embodiment of the present invention which provides for some diagnostic capability. In this embodiment specific reference vectors are defined representing specific conditions such as myocardial infarction. This region in pattern space defines a specific heart condition and can be obtained by inputting electrocardiograph signals which are known to represent the operation of a heart during the specific condition. In this embodiment during the monitoring phase, if the electrocardiograph signal values fall outside the threshold of normality and inside the region of abnormality, the apparatus can give an indication of the specific heart condition which has arisen.

Whilst FIG. 11 illustrates only a single region in pattern space representing a single specific heart condition, clearly this approach can be used to define many different regions in pattern space representing many different specific heart conditions.

The neural computer is thus capable of generating a signal which can cause an alarm to be raised either audibly or visually. One embodiment of the present invention also provides the capability to equal the audible or visual warning device to give an indication of the specific heart condition which has arisen if this has been recognised by the neural computer.

Figure 12A:
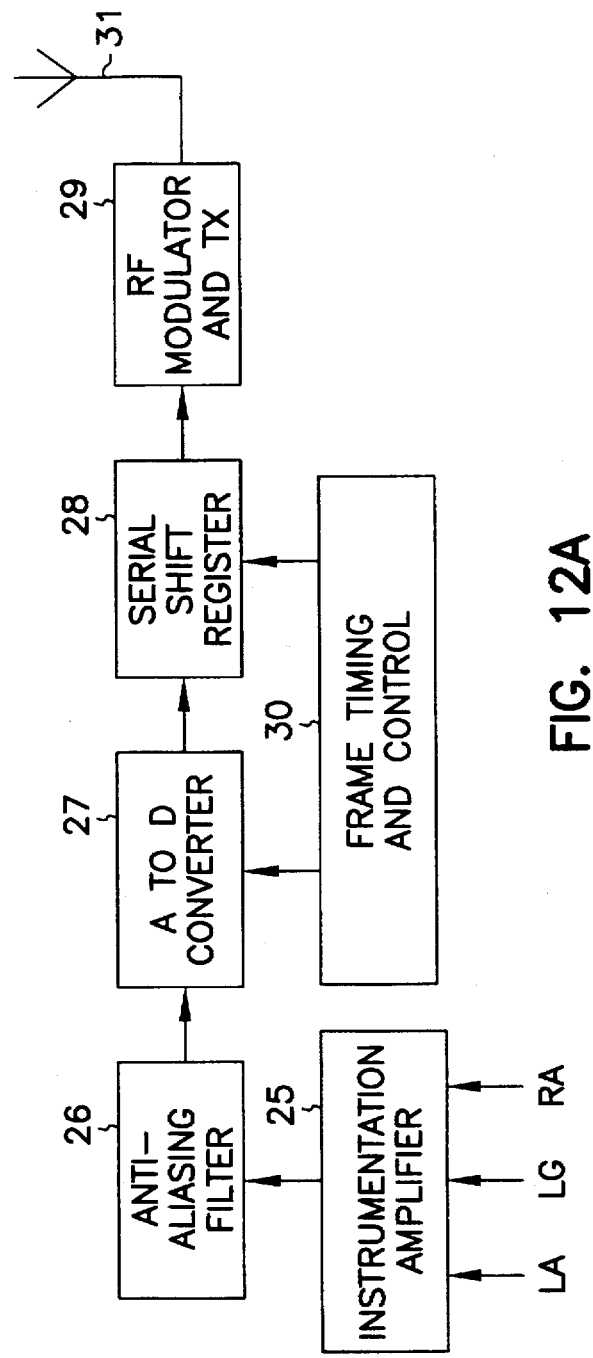
FIG. 12A is a schematic diagram of a transmission apparatus in accordance with a sixth embodiment of the present invention.
Figure 12B:
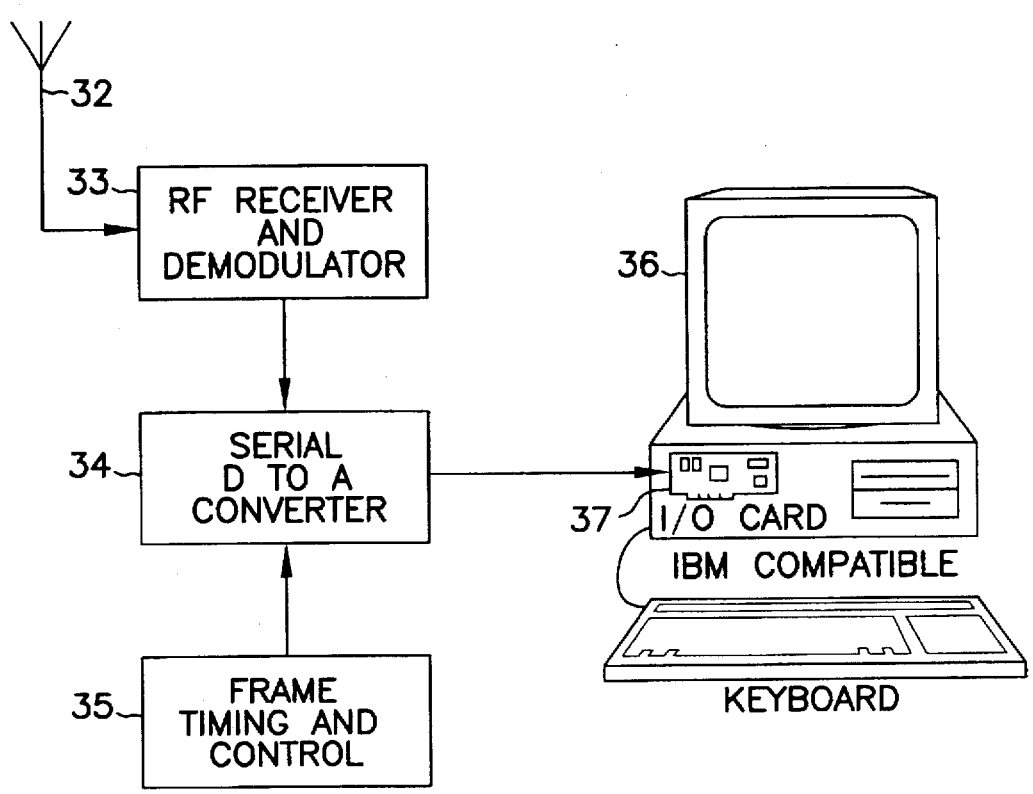
FIG. 12B is a schematic diagram of the receiver apparatus in accordance with the sixth embodiment of the present invention.

Referring now to FIGS. 12A and 12B, a sixth embodiment of the present invention will now be described. FIG. 12A illustrates a transmitter module which can be carried by a patient. Conventional electrocardiograph signals LA, LG, RA are received by the instrumentation amplifier 25 which amplifies the differential signal and outputs it to an anti-alias filter 26 to move high frequencies which can cause sampling errors. The filtered signal is then passed on to an analogue to digital converter 27 and the digitised signal is then input to a serial shift register 28. The analogue to digital converter 27 and the serial shift register 28 are under the control of the frame timing and control unit 30. The output of the serial shift register 28 is then input to the RF modulator and transmitter 29 for transmission of the electrocardiograph signal on the antenna 31 to the remote space station.

FIG. 12B schematically illustrates the remote base station. The transmitted electrocardiograph signal is picked up by the antenna 32 and passed to the RF receiver and demodulator 33. The demodulated electrocardiograph signal is converted to a serial analogue signal by the serial digital to analogue converter 34 under the control of the frame timing and control unit 35. The serial analogue signal is then input to a input/output card 37 within the computer 36. In this embodiment the computer is an IBM (trademark) compatible computer and the input/output card is the Lab-PC+ multiple channel analogue and digital I/OCARD available from National Instruments. The data acquisitional software used is the NI/DAQ software available from National Instruments.

A description will now be made of the circuits forming the transmitter and receiver units illustrated in FIGS. 12A and 12B.

Figure 13A:
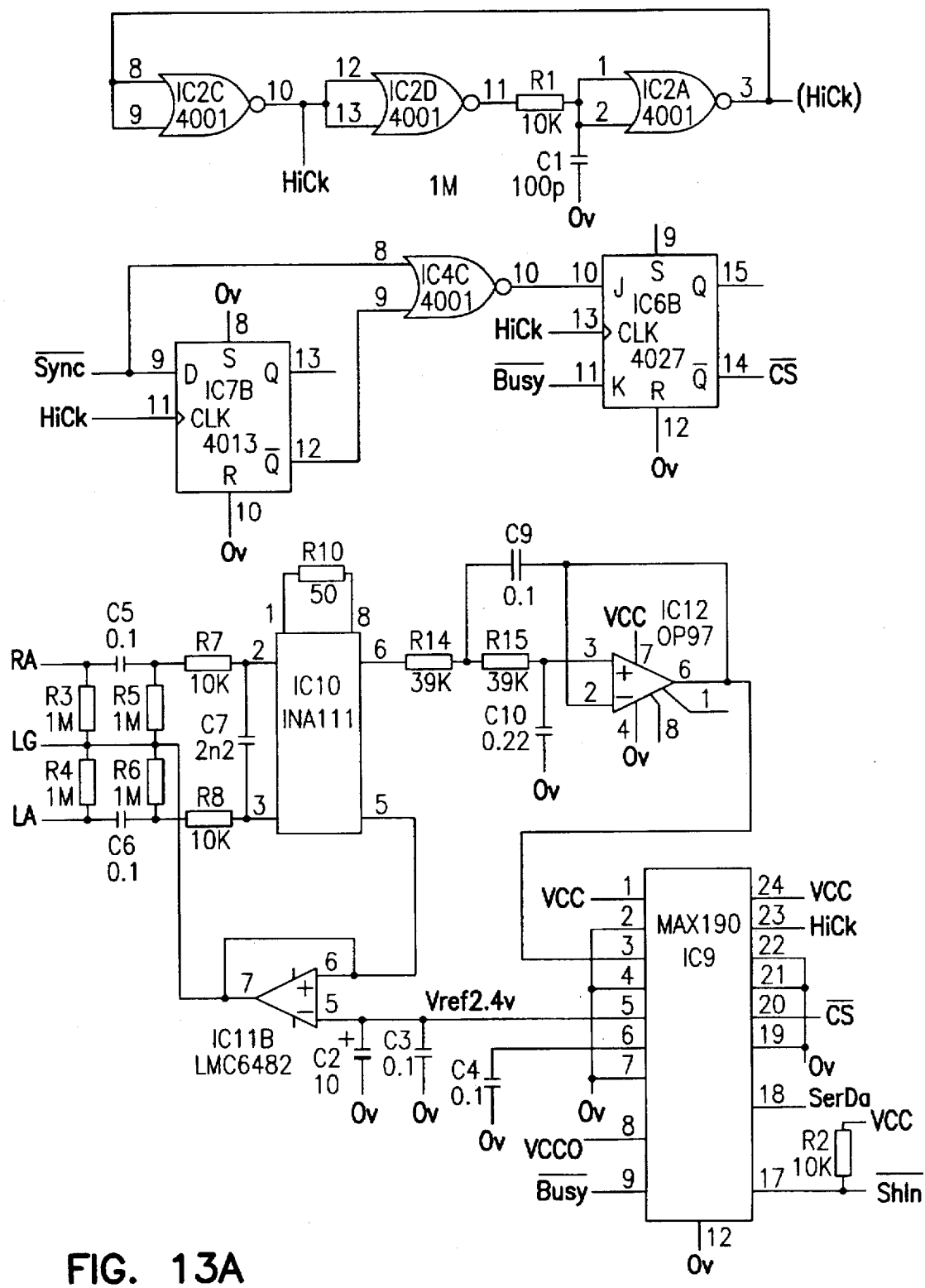
FIGS. 13A and 13B are circuit diagrams of the transmitter apparatus illustrated in FIG. 8A.
Figure 13B:
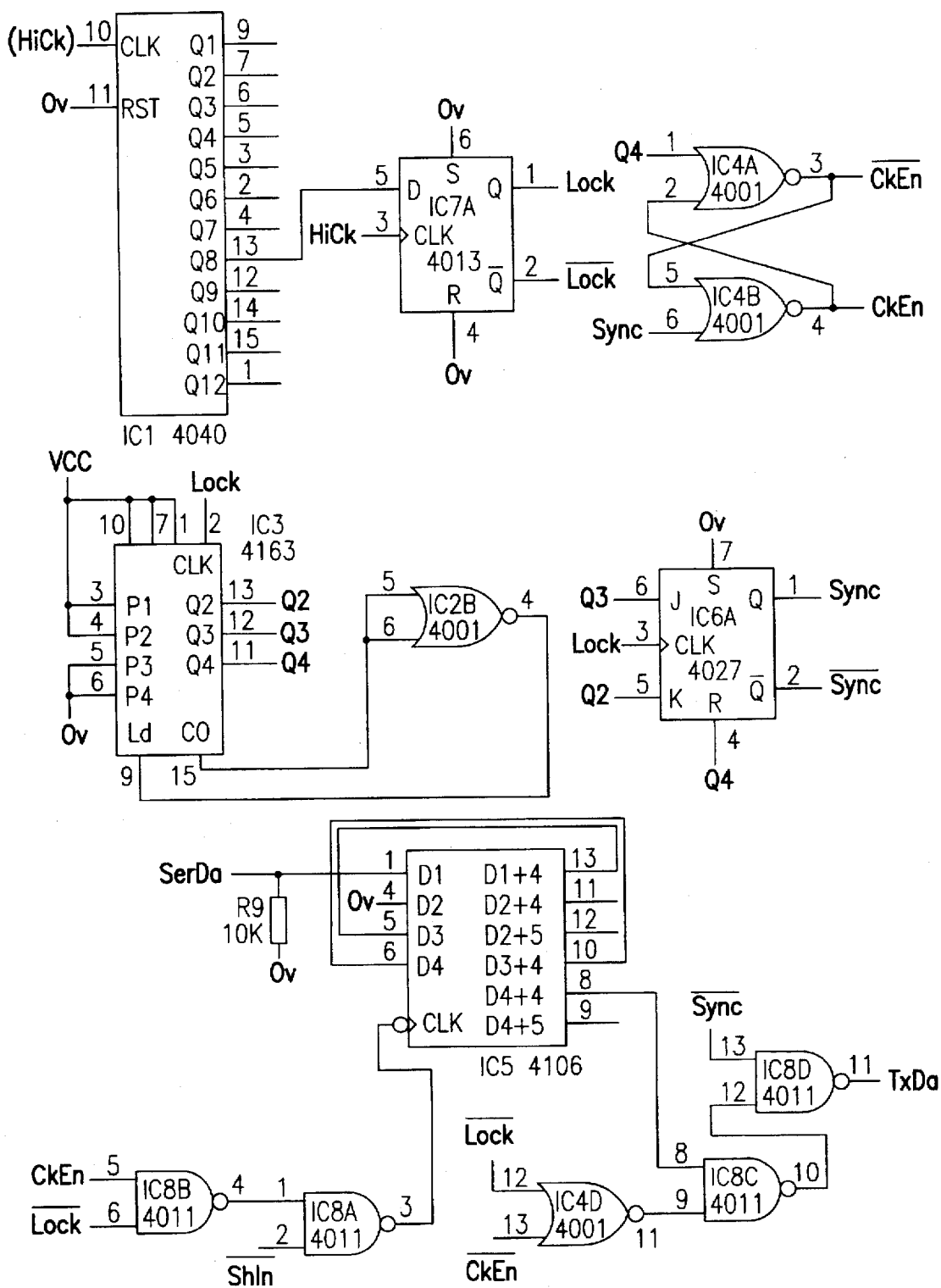

FIGS. 13A and 13B illustrate the circuit diagram of the instrumentation amplifier 25, the anti-aliasing filter 26, the analogue to digital converter 27, the serial shift register 28, and the frame timing and control unit 30 of FIG. 8.

The electrodes placed on the patient detect a differential signal of amplitude approximately one millivolt. This signal is then passed via capacitors C5 and C6 and remove any DC component and then through a low pass filter comprising resistors R7, R8 and capacitor C7. DC restoration of the incoming signal is assured by providing 1Mō leakage resistance R3, R4, R5 and R6 to the earth point. Very high input impedance instrumentation amplifier IC10 having again set to 2000 is used to amplifier the electrocardiac signal. The output of IC10 is passed through a unity gain low pass filter IC12 which has a roll-off frequency less than 100 Hz. The output of the low pass filter IC12 is input to a 12 bit analogue to digital converter IC9. The analogue to digital converter is configured to give a serial digital output of 12 bit accuracy but only the ten most significant bits of data are used.

The analogue to digital conversion cycle commences when the chip select (CS) signal of pin 20 is taken low. Immediately following this the analogue to digital converter takes pin 9 low indicating it is busy. When the conversion is complete the busy signal will be taken high, and via a J-K flip-flop IC6. The (CS) signal will also be taken high.

As each stage of the successive approximation analogue to digital conversion occurs, a data bit and a clock edge is generated by the analogue to digital converter with the most significant bit first. These are output on pins 18 and 17 respectively. The serial data (SerDa) and clock (shIn) are routed to a shift register IC5 and the data is clocked into the shift register at the HiCk rate of 1.5 microseconds per bit.

The frame timing and logic control comprises four main blocks: the oscillator and divider, the counter, the gating logic, and the shift register. The oscillator and divider comprises three inverters IC2A, IC2C and IC2D connected in series together with a resistor R1 and a capacitor C1 is connected ground between inverters IC2A and IC2D. This forms an oscillator running at 667 KHz which is the HiCk frequency. The output of inverter IC2A is fed to the asynchronous binary divider IC1 which divides HiCk by 256 to produce a low frequency clock LoCk running at 2.6 kHz. A D-type flip-flop IC7A is used to synchronise the output of the divider to HiCk.

The counter comprises a synchronous programmable counter IC3 set to divide by thirteen. It does this by being preset to three and then counting to fifteen whereupon the carry out once began presets the counter to three. This creates the data frame rate of 200 frames per second from the 2600 Hz clock.

The start of each frame is indicated by a Sync pulse LoCk beats wide. This is generated by a J-K flip-flop IC6A. When the output of Q3 of the counter IC3 goes high, on the count transition from three to four, the J input of the J-K flip-flop IC6A is taken high and on the next LoCk rising edge, the Q output Sync of the J-K flip-flop IC6A goes high. Two counts later the Q2 output of the counter IC3 goes high as the counter goes from five to six and the K input of the J-K flip-flop IC6A goes high. On the next rising edge of LoCk the Q output of the J-K flip-flop clocks back low. To prevent the J-K flip-flop IC6A from toggling on the next LoCk edge, the J-K flip-flop IC6A is held reset when the output Q4 of the counter IC3 goes high. Sync is used to start an analogue to digital conversion by having a leading edge detector, comprising an inverter IC4C and a J-K flip-flop IC7B generate a one beat pulse which puts the J-K flip-flop IC6B high and CS low to start the analogue to digital conversion. A set-reset flip-flop is created from the inverters IC4A and IC4B to provide gating for ten beats of LoCk by setting the flip-flop when the Q4 output counter IC3 goes high, count eight, and resetting the flip-flop low when the Sync goes high, count three. The output, clock enable (CkEn) is used to gate the clock at the shift register IC5.

The shift register IC5 is configured as a twelve bit shift register. The analogue to digital converter IC9 generates the twelve clock edges at 1.6 microsecond intervals as it completes a conversion and each data bit is clocked into the shift register IC5 using this. The data is clocked out at the much slower rate of 2600 Hz. LoCk is gated with CkEn by the inverter IC8B to shift out the data in the shift register IC5. The serial data stream is mixed with the Sync pulse on the inverter IC8D and is gated with inverted LoCk from the inverter IC4D so that half width data pulses are generated in the serial output stream. Only ten LoCk edges are gated into the shift register IC5 so that the least significant two bits of data are ignored.

In this embodiment a proprietary low powered radio module is used for data transmission. This operates at 433 MHz or 458 MHz and operates FM. Modulation band width is in the region of 4000 baud and so is capable of handling 2600 baud data rate in this particular configuration.

The circuit has been implemented as a low power design so that it can operate from low capacity batteries.

Figure 14A:
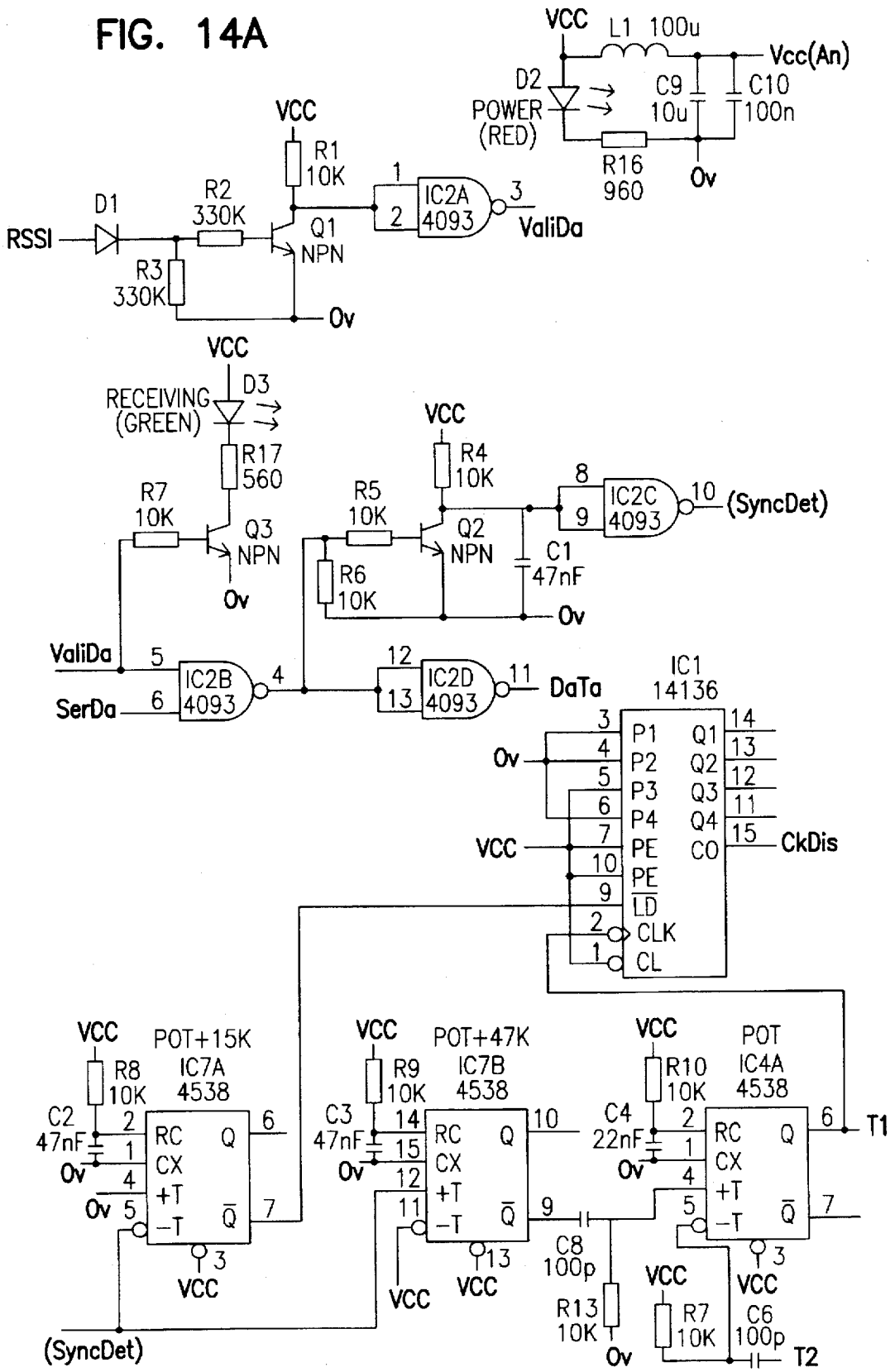
FIGS. 14A and 14B are circuit diagrams of the receiver apparatus for generating the serial analogue data in the receiver apparatus of FIG. 8B.
Figure 14B:
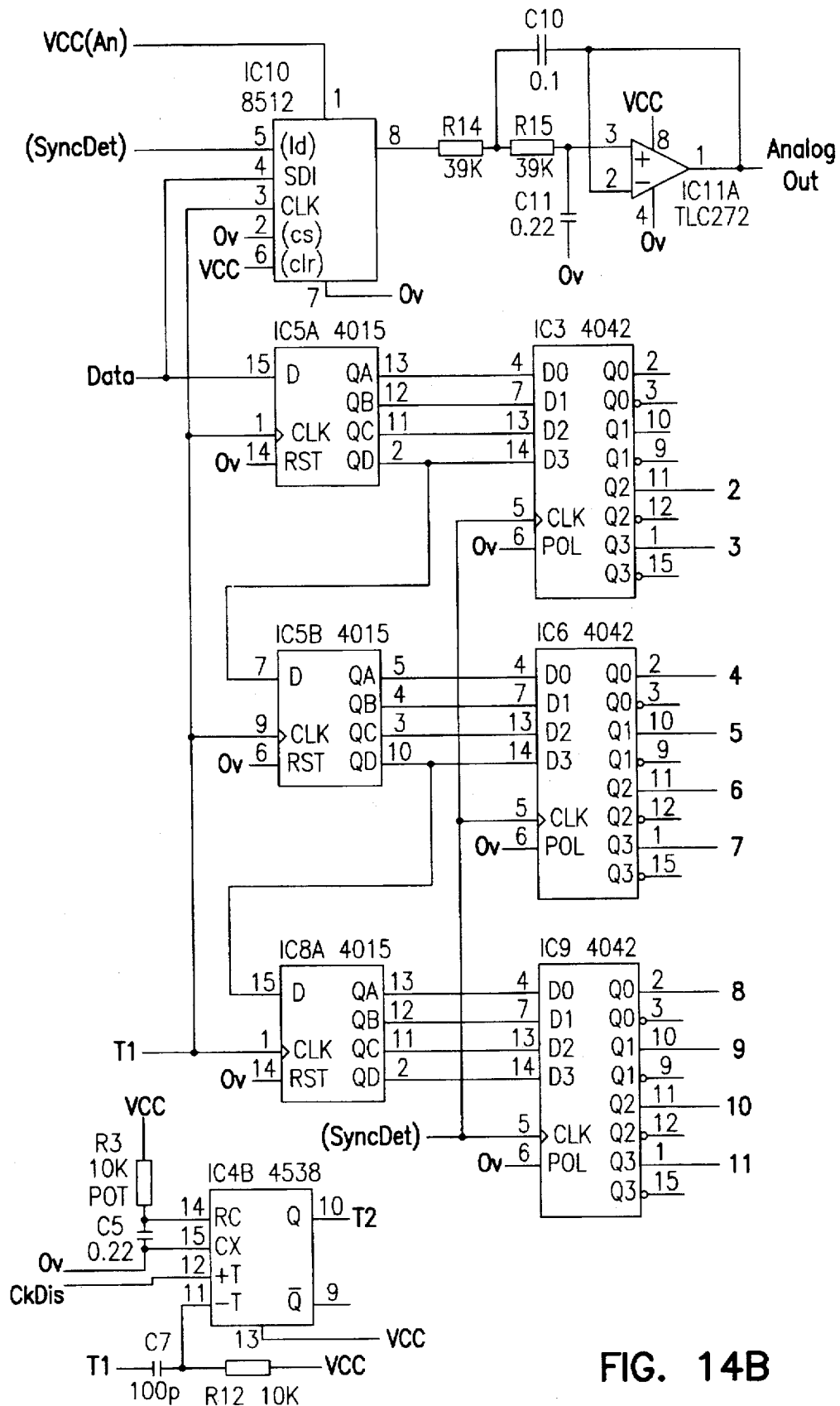
Figure 15:
FIG. 15 is a diagram of the received electrocardiograph signal.

Referring now to FIGS. 14A and 14B, the receiver and decoder circuit comprises a proprietary FM receiver with two outputs, a signal out and a received signal strength indicator (RSSI). If RSSI is not present the decoder circuit is held reset. The RSSI signal is input to a diode D1 to provide a threshold level for the cut-off as the strength falls but before data corruption can occur. The transistor Q1 is used to switch the signal into the submit trigger IC2A to produce a valid data signal ValiDa. A green LED D3 is used to indicate the presence of this signal. The valid data signal is also used to gate the serial data so that only valid data is accepted. The transistor Q2 is a Sync detector. As long as data pulses are present capacitor C1 will be held discharged. Whenever a Sync pulse occurs which is two beats wide and therefore longer than any other pulse, the voltage across the capacitor C1 rises to the threshold of the schmitt trigger IC2C and (SyncDet) goes low. The signal goes high on the trailing edge of Sync.

The (SyncDet) signal is input to monostables IC7A and IC7B. The monostable IC7A is triggered on the leading edge of (SyncDet) and monostable IC7B is triggered on the training edge of (SyncDet). The monostables IC4A and IC4B are cross-coupled to form an oscillator. This technique is used in order to overcome any problems associated with oscillators where the first few cycles after being enabled will have a longer interval. With monostables the period of each cycle is accurately determined. The oscillator comprising the cross-coupled monostable IC4A and IC4B is triggered from the output of the monostable IC7B. The preset counter ICLA counts 12 cycles from the oscillator and then stops. It turns off the clock by gating off monostable IC4B. It is reset by IC7A and IC7B triggers monostable IC4A to start the clock.

The valid serial data is gated by schmitt trigger IC2B and IC2D and is fed to three and four bit shift registers IC5A, IC5B and IC8A which are connected to give twelve bits of serial register. Twelve clock cycles occur shifting in ten bits of data and two bits of Sync. The Sync bits are ignored and the bottom two least significant bits of the shift register are not used. The data is serially shifted in on one frame and on the (SyncDet) of the next frame the output buffers IC3, IC6 and IC9 are updated with data. Ten bits of data are available for input to the computer which can then use this data to perform data extraction and novelty detection. In the present embodiment this parallel data is not used.

Instead of using the parallel data a serial analogue output is used from the serial to analogue converter 10 and low pass filter connected amplifier IC11A. The serial digital to analogue converter provides a 0 to 5 volt output for serially clocked-in binary data wherein the data is clocked by T1. (SyncDet) is used as the load or update signal. The amplifier IC11A is used as a low pass filter to smooth the analogue signal.

Thus, in this embodiment electrocardiac signals are transmitted from the portable patient module to the remote base station for analysis. Reference will now be made to the method of analysis carried out by the sixth embodiment of the present invention with reference to FIGS. 15 to 23. This is carried out by a program operating in the PC.

Figure 16:
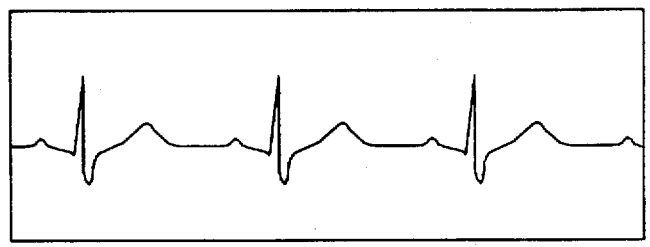
FIG. 16 is a diagram of the initial window of electrocardiograph data taken in the operation of the sixth embodiment of the present invention.
Figure 17:
FIG. 17 illustrates the method of identifying the R wave peak.
Figure 18:
FIG. 18 illustrates the method of centering a one second window around the R wave peak.
Figure 19:
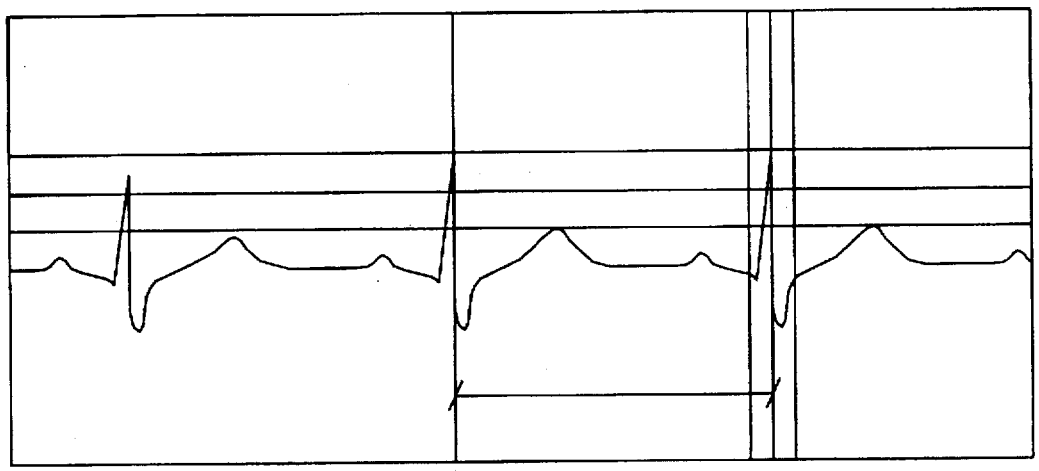
FIG. 19 illustrates the method of determining the heart rate.
Figure 22A:
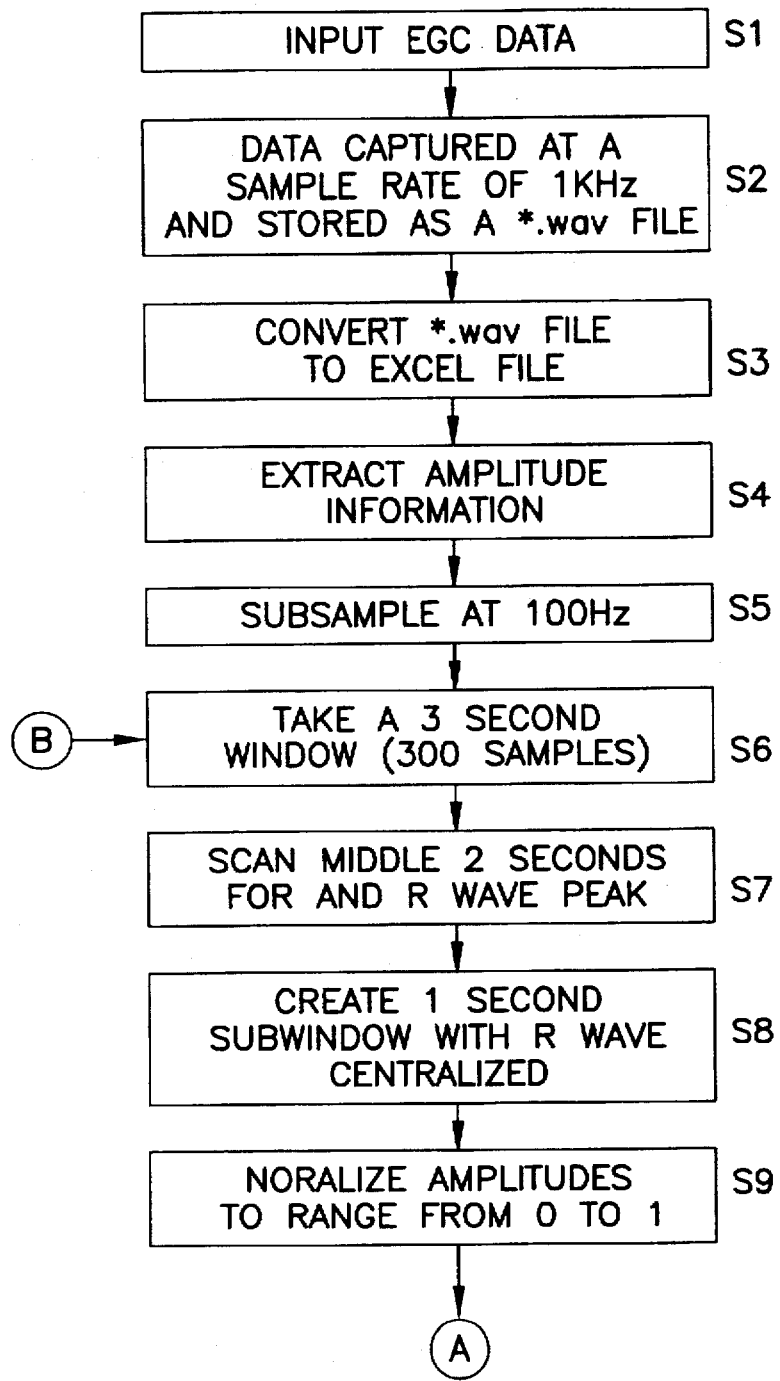
FIGS. 22A and 22B are flow diagrams illustrating the operation of the sixth embodiment.
Figure 22B:
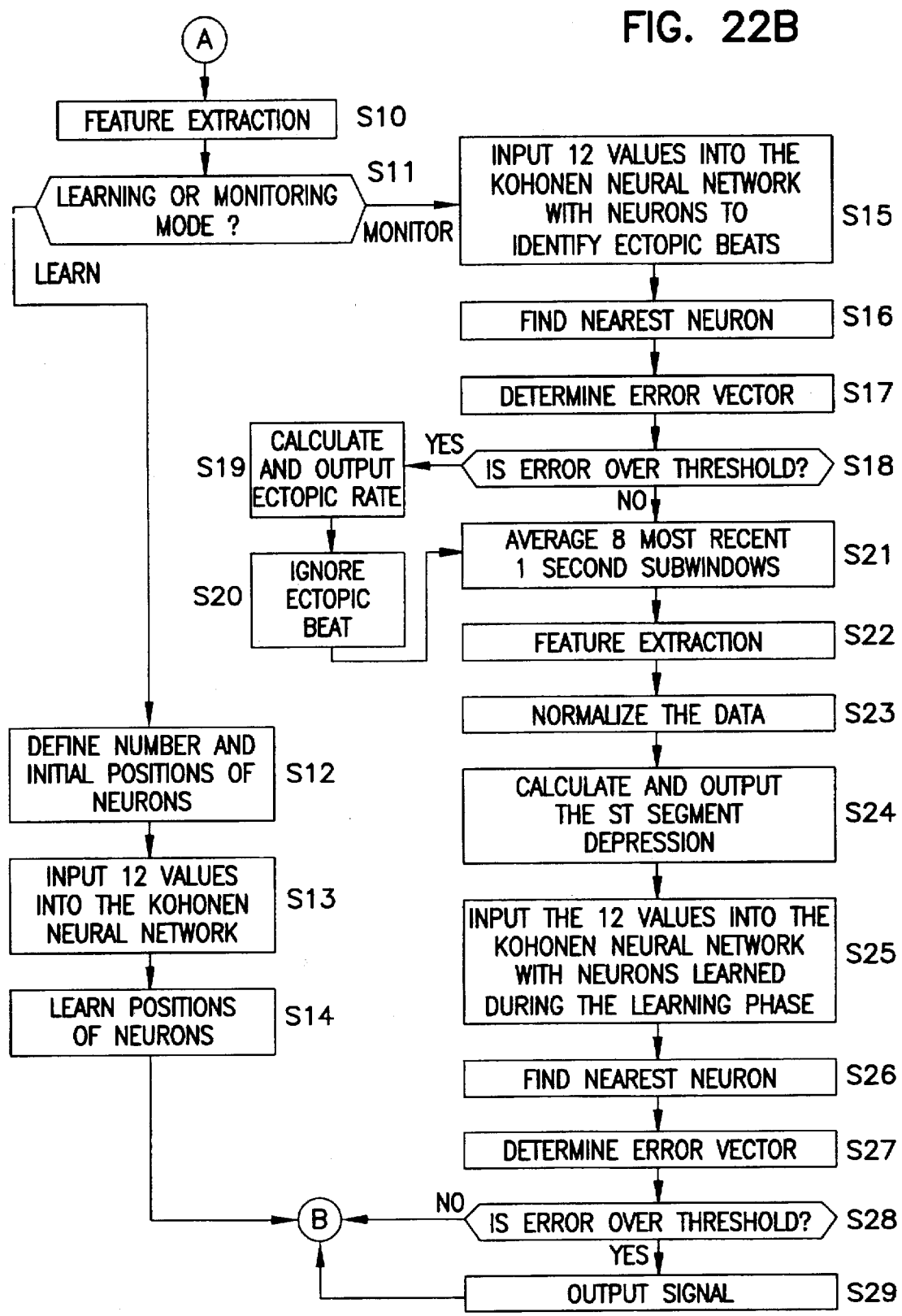
Figure 23:
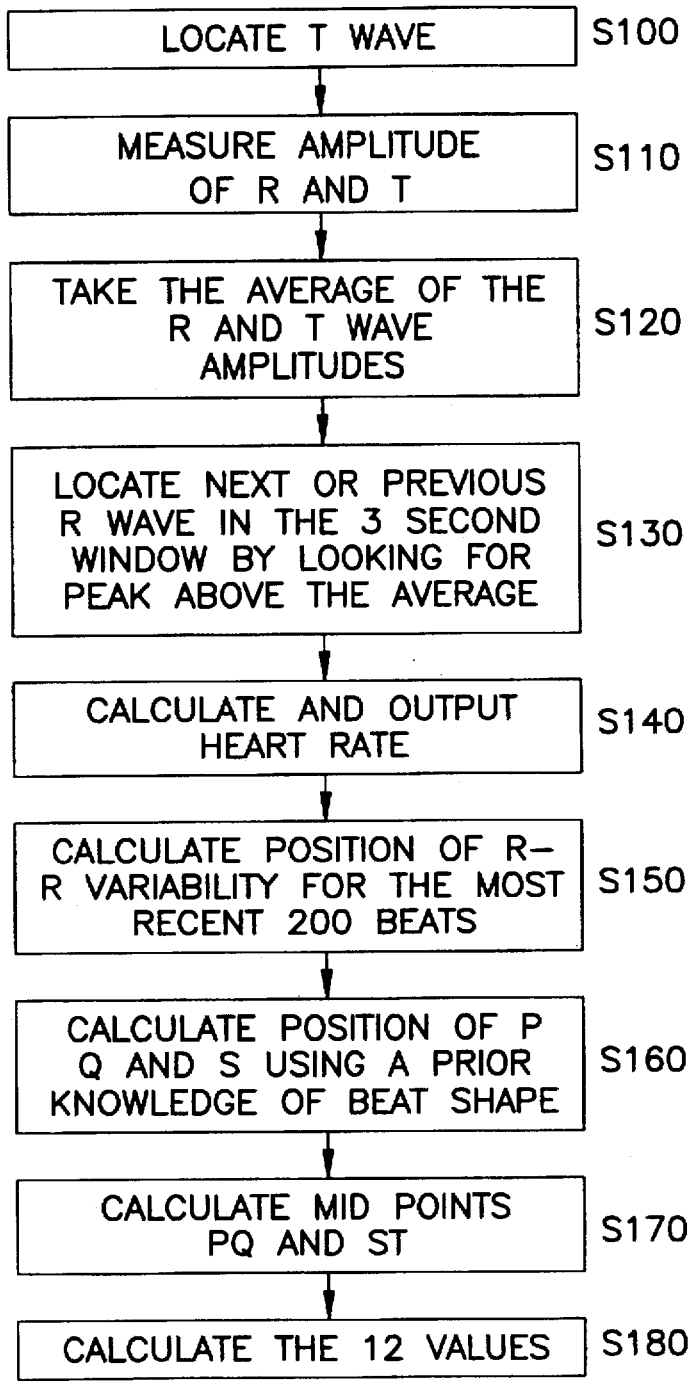
FIG. 23 is a flow diagram illustrating the feature extraction step.

FIG. 22A and 22B illustrate the method of analysis of this embodiment of the present invention. In step S1 electrocardiograph data is input in the form illustrated in FIG. 15. The data is captured at a sample rate of 1 KHz and stored as a binary *.WAV file in step S2. The binary *.WAV file is converted to an Excel (trademark) file in step S3 and in step S4 the amplitude information is extracted. In step S5 the data is sub-sampled at frequency of 100 Hz. In step S6 a three second window ie. 300 samples is taken as shown in FIG. 16. In step S7 the middle two seconds are scanned for an R wave peak. The peak is identified as shown in FIG. 17 and in step S8 a one second window is created with the R wave centralised as shown in FIG. 18. In step S9 the entire three second window is then normalised such that the one second window has amplitudes ranging from 0 to 1. The next step as illustrated in FIG. 22B is step S10 which is feature extraction. FIG. 23 illustrates the steps in the feature extraction process. In step S100 the T wave is identified by finding the highest point within a window of preset distance from the R wave. This distance is defined by a priori information about electrocardiographs. In step S110 the amplitudes of both the S and R waves are then measure and in step S120 the mean value of the two is taken and used in step S130 to locate the next or previous R wave in the three second window by looking for a peak above the calculated average value. The larger section of the three second window to either side of the initially located R wave is scanned from the R wave to locate the next point at which the amplitude is higher than the mean value. A window is then placed around this location to locate the next R wave. FIG. 19 illustrates this process.

From the measured interval between R waves, in step S140 the heart rate in beats per minute is calculated. The value calculated is a discreet value which is not smoothed by averaging over time. In step S150 the R to R variability i.e. the variation in heart rate is calculated for the most recent 200 heartbeats and this is output together with the heart rate measurement.

The method then enters a series of steps designed to identify that a heartbeat shaped pattern is present and to locate irregular beats such as a ventricular ectopic beat or an artifact. A ventricular ectopic beat occurs when the conduction path through the heart is initiated from a rogue node in the ventricles. It is important to locate such beats for heart stress diagnosis, but must be considered as spurious with regards to monitoring heart conditions.

The main concept behind this part of the method is to transfer the signal from the time dimension to a dimension offering greater separation of signal types. This is achieved in this particular embodiment by segmentation of the signal. However, transforms such as the Fourier transform or more particularly the Wavelett transform may be employed in order to generate the requirement values.

Figure 21:
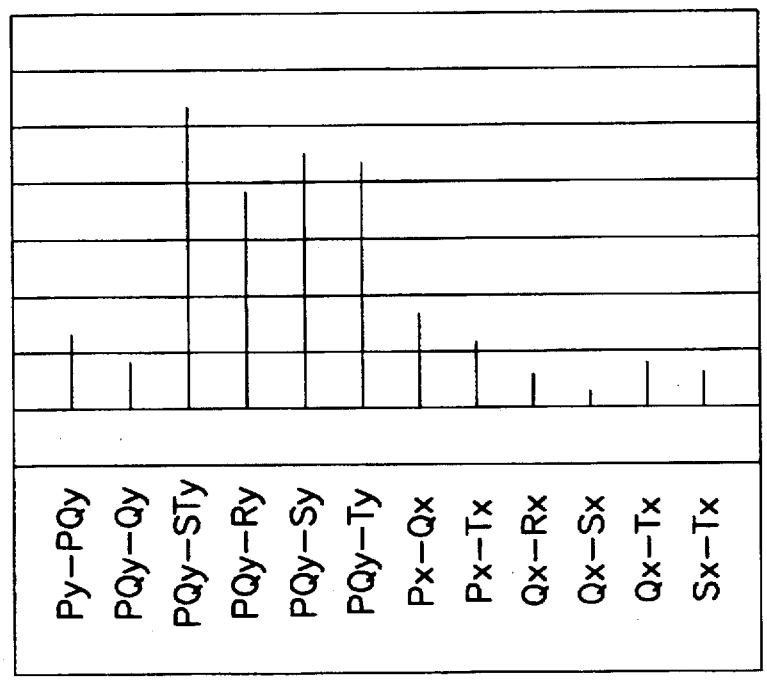
FIG. 21 illustrates a display of the twelve values obtained.
Figure 20A:
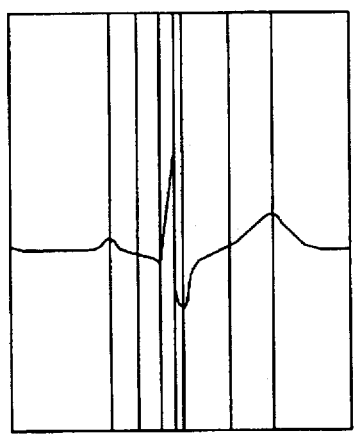
FIGS. 20A, 20B and 20C illustrate the identification of the twelve values from the electrocardiograph trace.
Figure 20B:
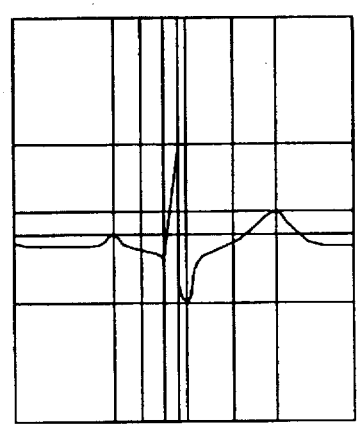
Figure 20C:
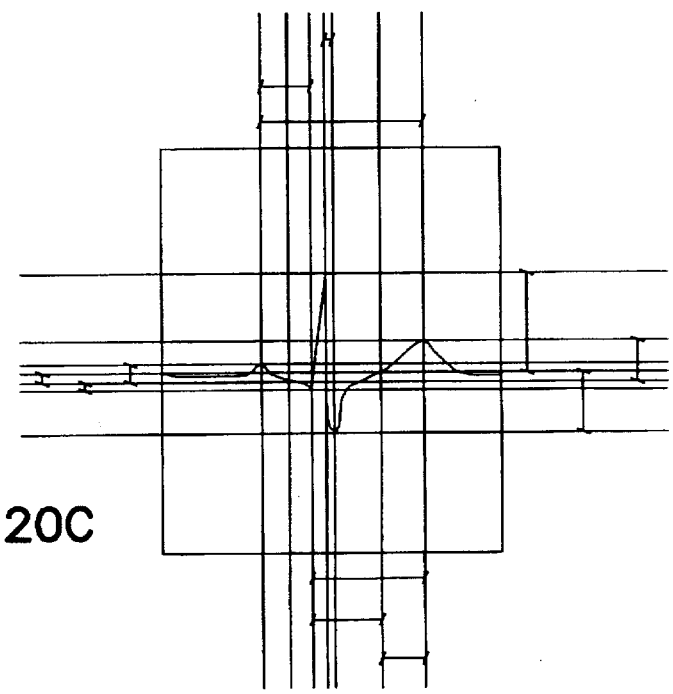

In step S160 the positions of the PQ and S waves are calculated using a priori knowledge of beat shape. The midpoint of the P and Q waves occur during what is termed the P—R interval. This may be considered as a base line from which to measure amplitudes. The midpoint of the S and T waves has diagnostic important with regard to the recovery period of the ventricles. Thus in step S170 the midpoints PQ and ST are determined as shown in FIG. 20A. FIG. 20B shows the calculation of the amplitude of these points and in FIG. 20C the calculation of twelve values carried out in step S180 is illustrated. FIG. 21 illustrates the twelve values which can be obtained from an ECG trace.

The twelve points which are taken to analyze the wave form are

° $P_{amplitude} - PQ_{amplitude}$|
|$PQ_{amplitude} - Q_{amplitude}$|
|$PQ_{amplitude} - ST_{amplitude}$|
|$PQ_{amplitude} - R_{amplitude}$|
|$PQ_{amplitude} - S_{amplitude}$|
|$PQ_{amplitude} - T_{amplitude}$|
|$P_{time} - Q_{time}$|
|$P_{time} - T_{time}$|
|$Q_{time} - R_{time}$|
|$Q_{time} - S_{time}$|
|$Q_{time} - T_{time}$|
|$S_{time} - T_{time}$|

Having identified the twelve values representing the electrocardiograph signal, at step S11 it is determined whether the learning or monitoring mode is required. If the learning mode is required to determine the reference vectors or positions of the neurons in the Kohonen neural network, the learning phase is initiated in step S12 by the defining of the number and initial positions of the neurones. In step S13 the twelve values are then input into the Kohonen neural network which in step S14 adaptively learns the positions of the neurones. This will continue for each of the three second windows of the input ECG data identified in step S6.

If in step S11 it is determined that monitoring is required, the twelve values are input into the Kohonen neural network to identify ectopic beats in step S15. The principle of operation of the Kohonen neural network in both the learning and monitoring modes is described in the book by J Dayhoff. In step S16 the nearest neuron (reference vector) is determined and in step S17 the error vector between the input vector and the nearest reference vector is determined. In step S18 it is determined whether the error is above the predetermined threshold. If the threshold is exceeded in step S19 the ectopic rate is calculated and output and in step S20 the beat is marked as an ectopic beat so that it is ignored in the further processing of the electrocardiograph signal. The processing can then continue as if the threshold had not been exceeded in step S18 and in step S21 the eight most recent one second sub windows which do not include an ectopic beat are averaged by median averaging. In step S22 the feature extraction is once again carried out as shown in FIG. 23. In step S23 the twelve values are normalised using a pre-calculated mean and standard deviation for each value. The mean and standard deviation for each dimension is calculated for an arbitrary 100 data sets and each value is reduced by the mean value and divided by the standard deviation in order to normalise the values.

In step S24 the ST segment depression has calculated and output. The ST segment depression holds diagnostic information with regards to the recovery ability of the ventricles. Thus, ST segment depression can be used as an indication of overall heart stress level.

The twelve normalised values are then input into the Kohonen neural network in step S25. The Kohonen neural network has neurons which were learnt during the learning phase (steps S12, S13 and S14). In step S26 the nearest neuron to the input vector is determined and in step S27 the error vectors are determined. In step S28 it is determined whether the threshold is exceeded and if so an output signal is generated in step S29 indicating novelty. In step S29 also the error vector determining step S27 can be output.

If the threshold is not exceeded once the signal has been output in step S29 it has been determined that the threshold has been exceeded, the next three second window can be analyzed i.e. the process can return to step S6. In the method of operation of the sixth embodiment five outputs are generated and these are heart rate in beats per minute, heart rate variability (R—R variability), ectopic rate, ST segment depression, and the output signal of the Kohonen neural network analysis. Each of these five different measurements are a significant indicator of heart stress and these values can be weighted and combined to give an overall level of heart stress. The actual weighting applied to these signals are application dependent. The requisite weighting can be calculated using a neural network such as the multi-layered perception. The operation of this network is also described in the book by J Dayhoff.

The ability to monitor the general level of stress experienced by the heart will enable a graded output vector of heart stress. This enables the system to have wide ranging applications.

Figure 24:
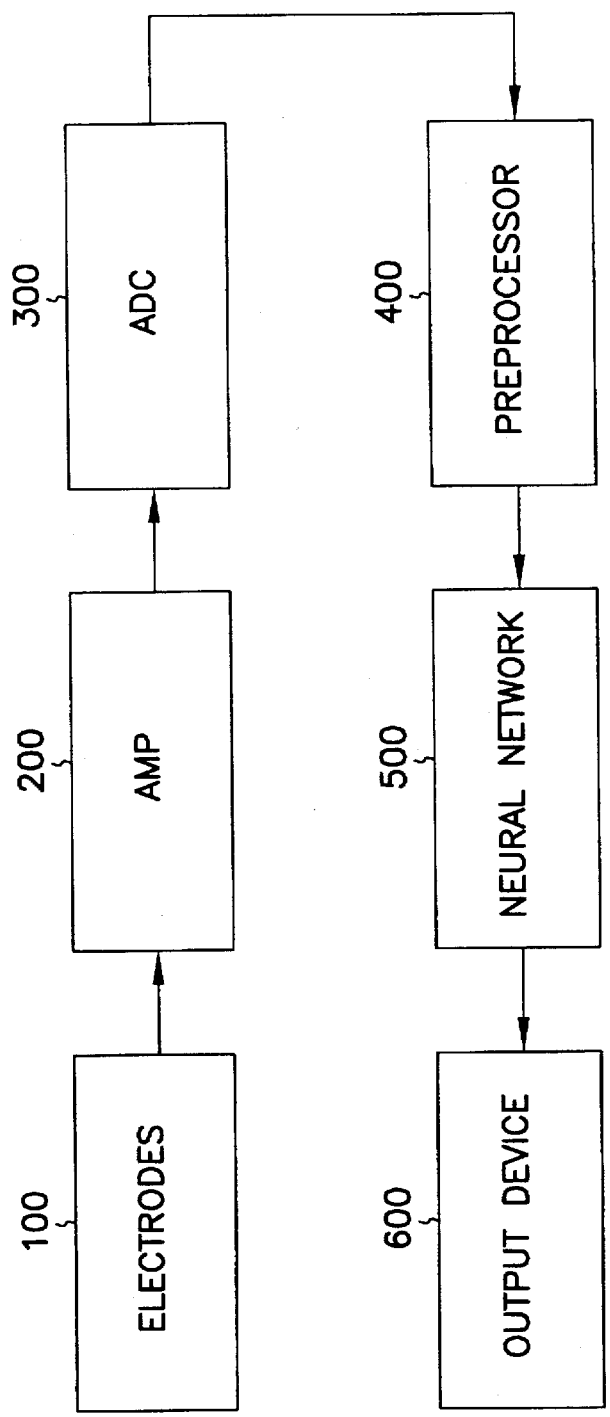
FIG. 24 is a schematic diagram of a seventh embodiment of the present invention.

Referring now to FIG. 24, this is a schematic drawing of a seventh embodiment of the present invention wherein all the features of the signal processing and analysis are carried out within a single unit which can be a portable unit. The electrocardiograph signal from the electrodes 100 is passed to an instrumentation amplifier 200 and thence to an analogue to digital converter 300. The digitised signal is then passed to the preprocessor 400 for preprocessing the signal. The preprocessed signal is then passed to the neural network 500 for analysis as hereinbefore described. The output of the neural network is then output to an output device 600 which can comprise a display and/or audible output unit. The output device can also trigger the storage of any of the electrocardiograph signals.

Although the present invention has been described with reference to specific embodiments, it should be appreciated that the present invention is not limited to such embodiments and it should be recognised that various modifications are possible within the scope of the invention claimed. For instance, the visual or audible output can indicate the level of stress experienced by the heart, or could more specifically provide a warning when specific heart conditions are detected or an undesirable change in the operation of the heart is detected for a patient. Also, the detection of a particular stress level, the detection of a change in operation of the heart, or the detection of a specific heart condition by the neural network can be used to trigger the recording of the electrocardiograph trace for analysis by a suitably trained person. Also, the number of times that such events occur can be logged and additionally the patient can be provided with an indicated device to log a point in time if and when they feel as well. This will provide additional information to allow the identification of heart conditions. Further, although reference has been made throughout to the use of the Kohonen neural network, the present invention is applicable to any equivalent neural network which can provide for the analysis of the electrocardiograph derived values.

I claim:

1. Heart monitoring apparatus comprising:

detection means for obtaining an electrocardiograph signal from a patient during a monitoring phase, preprocessing means for processing said electrocardiograph signal to enhance the salient features of the electrocardiograph signal and suppress the noise, and to generate a plurality n of values representative of the features of said electrocardiograph signal, storage means for storing a plurality m of n dimensional reference vectors;

Kohonen neural network means for receiving said plurality of values during the monitoring phase, for forming an n dimensional vector from said plurality of values and for comparing said n dimensional vector with said stored plurality m of n dimensional reference vectors defining an n dimensional Kohonen feature map to determine the proximity of said n dimensional vector to said reference vectors, and output means for outputting a signal if said Kohonen neural network means determines that said n dimensional vector is within or beyond a threshold range of said reference vectors.

2. Heart monitoring apparatus as claimed in claim 1 wherein said Kohonen neural network means includes means to receive, during a learning phase, a plurality of reference values representative of the features of a reference electrocardiograph signal, means to generate an n dimensional Kohonen feature map having said plurality m of reference vectors, and means to store said reference vectors in said storage means.

3. Heart monitoring apparatus as claimed in claim 2 wherein said detection means includes means to obtain the reference electrocardiograph signal from the patient during the learning phase; said Kohonen neural network means includes means to, during the monitoring phase, determine whether the n dimensional vector lies outside a predetermined range of said reference vectors; and said output means includes means to output said signal if said Kohonen neural network means determines that said n dimensional vector lies outside said predetermined range.

4. A heart monitoring apparatus as claimed in claim 2 including reference input means to input said reference electrocardiograph signal to said preprocessing means.

5. Heart monitoring apparatus as claimed in claim 4 wherein input means includes means to input said reference electrocardiograph signal representing normal range of operation of the heart; said Kohonen neural network means includes means to determine whether the n dimensional vector lies outside a predetermined range of said reference vectors; and said output means includes means to output said signal if said Kohonen neural network means determines that said n dimensional vector lies outside said predetermined range.

6. Heart monitoring apparatus as claimed in claim 4 wherein said input means includes means to input at least one abnormal said reference electrocardiograph signal representing at least one known heart condition; said Kohonen neural network means includes means to determine whether the n dimensional vector lies within a predetermined range of the abnormal reference vectors; and said output means includes means to output said signal if said Kohonen neural network means determines that said n dimensional vector lies inside said predetermined range.

7. Heart monitoring apparatus as claimed in claim 2 wherein said Kohonen neural network means includes means to, in the learning phase, receive a second plurality of reference values representative of features of an electrocardiograph signal indicative of a specific heart condition, to generate a plurality of abnormal reference vectors in said n dimensional Kohonen feature map; and means to in the monitoring phase, compare said n dimensional vector with said plurality of abnormal reference vectors to determine whether said n dimensional vector lies within a predetermined range of said abnormal reference vectors;

said apparatus including heart condition warning means responsive to said output signal for generating a warning that said patient has said specific heart condition if said Kohonen neural network means determines that said n dimensional vector lies within said predetermined range of said abnormal reference vectors.

8. Heart monitoring apparatus as claimed in claim 1 including vector inputting means for inputting said plurality m of reference vectors defining said n dimensional Kohonen feature map to said storage means.

9. Heart monitoring apparatus as claimed claim 1 wherein said preprocessing means includes means to carry out feature extraction to extract important features from said electrocardiograph signal, and to use said features to form said plurality n of values.

10. Heart monitoring apparatus as claimed in claim 9 wherein said preprocessing means includes means to identify the peaks in said electrocardiograph signal and to measure the peak values to form said plurality n of values.

11. Heart monitoring apparatus as claimed in claim 10 wherein said preprocessing means includes means to identify points midway between peaks and to measure the values of the electrocardiograph signal at said points to include the values in said plurality n of values.

12. Heart monitoring apparatus as claimed in claim 11 wherein said preprocessing means includes means to identify the P, Q, R, S and T peaks and mid points between the P and Q peaks and the S and T peaks in said electrocardiograph signal, and to use the values of the signal at the identified peaks and points to form said plurality n of values.

13. Heart monitoring apparatus as claimed in claim 1 wherein preprocessing means includes means to perform a transform of said electrocardiograph signal.

14. Heart monitoring apparatus as claimed in claim 13 wherein said preprocessing means includes means to perform a Fourier transform and/or a Wavelett transform of said electrocardiograph signal.

15. Heart monitoring apparatus as claimed in claim 1 wherein said Kohonen neural network means includes means to carry out said comparison and determination by determining the differences between said reference vectors and said n dimensional vector for each dimension, summing the individual dimensional differences and comparing the sum with a threshold difference value.

16. Heart monitoring apparatus as claimed in claim 1 wherein said Kohonen neural network means includes means to carry out said comparison and determination by mapping said n dimensional vector into said Kohonen feature map, calculating the differences therebetween by Pythagoras' law, and comparing said differences with at least one difference threshold.

17. Heart monitoring apparatus as claimed in claim 1 including filter means to remove distinctive irregular heartbeats from the electrocardiograph signal.

18. Heart monitoring apparatus as claimed in claim 17 including indicating means to indicate the occurrence of the distinctive irregular beats.

19. Heart monitoring apparatus as claimed in claim 18 wherein said indicating means comprises a low pass filter.

20. Heart monitoring apparatus as claimed in claim 17 or claim 17 wherein said filter means comprises a high pass filter.

21. Heart monitoring apparatus as claimed in claim 17 wherein said storage means stores a first set of n dimensional reference vectors for the identification of the distinctive irregular heartbeat, and a second set of n dimensional reference vectors for monitoring regular heartbeats;

said Kohonen neural network means includes means to, during the monitoring phase, initially compare the n dimensional vector with the stored first set of reference vectors to identify the distinctive irregular heartbeats, and to subsequently compare an n dimensional vector formed from regular heartbeats which exclude the distinctive irregular heartbeats with the second set of n dimensional reference vectors; and said output means includes means to output said signal if said Kohonen network means determines that said n dimensional vector formed from said regular heartbeats is within or beyond a threshold range of said second set of reference vectors.

22. Heart monitoring apparatus as claimed in claim 21 wherein said output means includes means to output a signal indicating the occurrence of a distinctive irregular heartbeat when said Kohonen neural network means determines that the n dimensional vector formed from the distinctive irregular heartbeat is within or beyond a threshold range of said first set of reference vectors.

23. Heart monitoring apparatus as claimed in claim 22 including averaging means responsive to the signal indicating the occurrence of a distinctive irregular heartbeat for averaging a plurality of said electrocardiograph signals or said plurality n of values for a plurality of regular heartbeats.

24. Heart monitoring apparatus as claimed in claim 23 including normalising means for normalising the averaged plurality of values by reducing the values by the mean values and dividing by the standard deviation.

25. Heart monitoring apparatus as claimed in claim 1 including averaging means for averaging a plurality of said electrocardiograph signals or said plurality n of values after removal of said distinctive irregular beats by said filter means.

26. Heart monitoring apparatus as claimed in claim 1 including alarm generating means for generating an alarm in response to the output signal of said output means.

27. Heart monitoring apparatus as claimed in claim 1 including data storage means for storing the electrocardiograph signal and/or the plurality of values over a period of time in response to the output signal of said output means.

28. Heart monitoring apparatus as claimed in claim 1 including postprocessing means to further process the output signal of said output means, wherein the output signal comprises an error vector, together with further data related to heart operation to provide an indication of heart stress.

29. Heart monitoring apparatus as claimed in claim 28 including means for providing said further data comprising at least one of heart rate, heart rate variation, rate of occurrence of distinctive irregular heartbeats such as ectopic beats, and the difference between the electrocardiograph signal value midway between the S and T peaks and the electrocardiograph signal value midway between the P and Q peaks.

30. Heart monitoring apparatus as claimed in claim 28 wherein said post processing means includes neural network means.

31. Heart monitoring apparatus as claimed in claim 30 wherein said neural network means comprise multi-layered perception means.

32. Heart monitoring apparatus as claimed in claim 1 including digitizing means for digitizing said electrocardiograph signal for input to said preprocessing means.

33. Heart monitoring apparatus as claimed in claim 1 wherein said detection means and said output means are remote from one another, the apparatus including communication means for airborne communications therebetween.

34. Heart monitoring apparatus as claimed in claim 33 wherein said detection means is provided in a portable housing arranged for attachment to the chest of said patient, said portable housing including transmitter means for transmitting signals to said output means; said output means being provided in a base station, said base station including receiver means to receive the transmitted signals.

35. Heart monitoring apparatus as claimed in claim 34 wherein said transmission means and said reception means are arranged to respectively transmit and receive said electrocardiograph signals, said base station including said preprocessing means, and said Kohonen neural network means.

36. Heart monitoring apparatus as claimed in claim 34 wherein said portable housing contains said preprocessing means, and said Kohonen neural network means; and said transmission and said reception means are arranged to respectively transmit and receive signals indicative of the proximity of said n dimensional vector to said reference vectors.

37. Heart monitoring apparatus as claimed in claim 33 wherein said detection means comprises electrodes for attachment to the chest of a patient, said apparatus including a portable housing adapted to be carried by the patient, said portable housing including transmitter means for receiving signals from said electrodes and for transmitting signals to said output means; said electrodes being connected to said housing by wires; said output means being provided in a base station, said base station including receiver means to receive the transmitted signals.

38. Heart monitoring apparatus as claimed in claim 1 including storage means for storage of the electrocardiograph signal or said plurality n of values for a predetermined period of time in response to the signal output by said output means.

39. A heart monitoring method comprising the steps of:
obtaining an electrocardiograph signal from a patient during a monitoring phase,
preprocessing the electrocardiograph signal to enhance the salient features of the electrocardiograph signal and suppress the noise, and to generate a plurality n of values representative of the features of the electrocardiograph signal,
forming an n dimensional vector from said plurality n of values,
comparing the n dimensional vector with a stored plurality m of n dimensional reference vectors defining an n dimensional Kohonen feature map to determine the proximity of the n dimensional vector to said reference vectors, and
outputting a signal if it is determined that the n dimensional vector is within or beyond a threshold range of said reference vectors.

40. A heart monitoring method as claimed in claim 39 including the steps during a learning phase of:
receiving a plurality of reference values representative of features of a reference electrocardiograph signal,
generating an n dimensional Kohonen feature map having said plurality m of reference vectors, and
storing said reference vectors.

41. A heart monitoring method as claimed in claim 40 including the steps of:
obtaining said electrocardiograph signal from said patient during the learning phase; and
during the monitoring phase determining whether the n dimensional vector lies outside a predetermined range of said reference vectors; and
outputting said signal if it is determined that said n dimensional vector lies outside said predetermined range.

42. A heart monitoring method as claimed in claim 41 including the steps of:
during the learning phase, inputting at least one abnormal said reference electrocardiograph signal representing at least one known heart condition; and
during the monitoring phase, determining whether the n dimensional vector lies within a predetermined range of the abnormal reference vectors, and outputting said signal if it is determined that said n dimensional vector lies inside said predetermined range.

43. A heart monitoring method as claimed in claim 40 including the steps of:
during the learning phase, obtaining said reference electrocardiograph signal representative of a normal range of operation of the heart, and processing the reference electrocardiograph signal to generate said plurality of reference values, and
during the monitoring phase, determining whether the n dimensional vector lies outside a predetermined range of said reference vectors, and outputting said signal if it is determined that said n dimensional vector lies outside said predetermined range.

44. A heart monitoring method as claimed in claim 40 including the steps of:
   in the learning phase, receiving a second plurality of reference values representative of features of an electrocardiograph signal indicative of a specific heart condition, and generating a plurality of abnormal reference vectors in said n dimensional Kohonen feature map; and
   in the monitoring phase, comparing said n dimensional vector with said plurality of abnormal reference vectors to determine whether said n dimensional vector lies within a predetermined range of said abnormal reference vectors, and generating a warning that said patient has said specific heart condition if it is determined that said n dimensional vector lies within said predetermined range of said abnormal reference vectors.

45. A heart monitoring method as claimed in claim 39 including the step of inputting and storing said plurality m of reference vectors defining said n dimensional Kohonen feature map.

46. A heart monitoring method as claimed in claims 39 wherein the preprocessing step comprises the steps of extracting important features from said electrocardiograph signal, and generating said plurality n of values from the extracted features.

47. A heart monitoring method as claimed in claim 46 wherein the processing step includes the steps of identifying the peaks in said electrocardiograph signal, and measuring the peak values to form said plurality n of values.

48. A heart monitoring method as claimed in claim 47 wherein said preprocessing step includes the steps of identifying points midway between peaks, and measuring the values of said electrocardiograph signal at said points to include the values in said plurality n of values.

49. A heart monitoring method as claimed in claim 48 wherein said preprocessing step includes the steps of identifying the P, Q, R, S and T peaks and mid points between the P and Q and the S and T peaks in said electrocardiograph signal, and using the values for the electrocardiograph signal at the identified peaks and points to form said plurality n of values.

50. A heart monitoring method as claimed in claim 39 wherein said preprocessing step includes the step of performing a transform of said electrocardiograph signal.

51. A heart monitoring method as claimed in claim 50 wherein said preprocessing step includes the step of performing a Fourier transform and/or a Wavelett transform of said electrocardiograph signal.

52. A heart monitoring method as claimed in claim 39 wherein the comparing step includes the step of determining the differences between said reference vectors and said n dimensional vector for each dimension, summing the individual dimensional differences, and comparing the sum with a threshold difference value.

53. A heart monitoring method as claimed in claim 39 wherein the comparing step includes the steps of mapping said n dimensional vector into said Kohonen feature map, calculating the differences therebetween by Pythagoras' law, and comparing said differences with at least one difference threshold.

54. A heart monitoring method as claimed in claim 39 including the step of removing distinctive irregular heartbeats from said electrocardiograph signal.

55. A heart monitoring method as claimed in claim 54 including the step of indicating the occurrence of the distinctive irregular beats.

56. A heart monitoring method as claimed in claim 54 including the step of averaging a plurality of said electrocardiograph signals or said plurality of values after removal of said distinctive irregular heartbeats.

57. A heart monitoring method as claimed in claim 54 including the steps of during the learning phase, storing a first set of n dimensional reference vectors for the identification of the distinctive irregular heartbeat, and a second set of n dimensional reference vectors for monitoring regular heartbeats;
   the comparing step comprising initially comparing the n dimensional vector with the stored first set of reference vectors to identify the distinctive irregular heartbeats, and subsequently comparing an n dimensional vector formed from regular heartbeats excluding the distinctive irregular heartbeats with said second set of n dimensional reference vectors; and
   the outputting step comprising outputting said signal if it is determined that said n dimensional vector formed from said regular heartbeats is within or beyond a threshold range of said second set of reference vectors.

58. A heart monitoring method as claimed in claim 57 wherein the outputting step includes the step of outputting a signal indicating the occurrence of a distinctive irregular heartbeat when it is determined that the n dimensional vector formed from the distinctive irregular heartbeat is within or beyond a threshold range of said first set of reference vectors.

59. A heart monitoring method as claimed in claim 58 including the step of averaging a plurality of said electrocardiograph signals or said plurality n of values for a plurality of regular heartbeats.

60. A heart monitoring method as claimed in claim 59 including the step of normalising the averaged plurality of values by reducing the values by the mean values and dividing by the standard deviation.

61. A heart monitoring method as claimed in claim 39 including the step of generating an alarm in response to the output signal.

62. A heart monitoring method as claimed in claim 39 including the step of storing the electrocardiograph signal and/or the plurality of values over a period of time in response to the output signal.

63. A heart monitoring method as claimed in claim 39 including the step of post processing the output signal, wherein the output signal comprises an error vector, together with further data related to heart operation to provide an indication of heart stress.

64. A heart monitoring method as claimed in claim 63 including the step of providing the further data comprising at least one of heart rate, heart rate variation, rate of occurrence of distinctive irregular heartbeats such as ectopic beats, and the difference between the electrocardiograph signal value midway between the S and T peaks and the electrocardiograph signal value midway between the P and Q peaks.

65. A heart monitoring method as claimed in claim 63 wherein the post processing is carried out by a neural network such as the multi-layered perception.

66. A heart monitoring method as claimed in claim 39 indicating the step of digesting the electrocardiograph signal prior to preprocessing.

67. A heart monitoring method as claimed in claim 39 wherein the obtaining step is carried out at one location and the output step is carried out at a second location remote from said first location, the method including providing airborne communications between the two locations.

68. A heart monitoring method as claimed in claim 67 wherein the electrocardiograph signals are obtained by a portable unit attached to the patient, and the output signal is provided at a base station remote from said portable unit.

69. A heart monitoring method as claimed in claim 68 wherein the electrocardiograph signals are transmitted to said base station where said preprocessing step, forming step, comparing step and output step take place.

70. A heart monitoring method as claimed in claim 68 wherein the obtaining and preprocessing steps take place in said portable unit, and said plurality n of values are transmitted to said base station.

71. A heart monitoring method as claimed in claim 39 including the step of storing the electrocardiograph signal and said plurality of values for a predetermined period of time in response to said output signal.

72. Heart monitoring apparatus comprising:

input means for receiving an electrocardiograph signal from a patient;

preprocessing means for processing said electrocardiograph signal to suppress the noise and extract important features of the electrocardiograph signal to obtain an n dimensional vector comprising a plurality n of values representative of the important features of said electrocardiograph signal;

storage means for storing a plurality m of n dimensional reference vectors;

neural network means for receiving said n dimensional vector, for comparing said n dimensional vector with said stored plurality m of n dimensional reference vectors defining an n dimensional volume to determine the proximity of said n dimensional vector to said n dimensional volume, and for outputting an indication of whether said n dimensional vector lies within or beyond a threshold range of said n dimensional volume.

73. Heart monitoring apparatus as claimed in claim 72 wherein said neural network means comprises Kohonen neural network means and said reference vectors form an n dimensional Kohonen feature map.

74. Heart monitoring apparatus comprising:

measuring means for measuring the activity of a patient's heart and outputting an electrocardiograph signal during a learning phase and a monitoring phase;

preprocessing means for processing said electrocardiograph signal to extract important features therefrom to generate an n dimensional vector comprising a plurality n of values representative of the features of the electrocardiograph signal; and Kohonen neural network means for, during the learning phase, using said n dimensional vector to generate an n dimensional Kohonen feature map with a plurality m of reference vectors defining a normal range of electrocardiograph features for said patient, and for during the monitoring phase, comparing said n dimensional vector with said plurality of m dimensional reference vectors defining the n dimensional Kohonen feature map to determine the proximity of said n dimensional vector to said reference vectors, and to output a signal if it is determined that said n dimensional vector is within or beyond a threshold range of said reference vectors.

* * * * *

UNITED STATES PATENT AND TRADEMARK OFFICE
CERTIFICATE OF CORRECTION

PATENT NO. : 5,749,367
DATED : May 12, 1998
INVENTOR(S) : Lee Gamlyn et al..

It is certified that error appears in the above-identified patent and that said Letters Patent is hereby corrected as shown below:

At Col. 1, line 15, please delete "undergoing" and insert --undergo--.

At Col. 4, line 21, please delete "analysis" and insert --analyze--.

At Col. 17, line 57, claim 9, please delete "claimed claim 1" and insert --claimed in claim 1--.

At Col. 18, line 39, claim 20, please delete "claim 17 wherein" and insert --claim 18 wherein--.

At Col. 21, line 23, claim 46, please delete "in claims 39" and insert --in claim 39--.

Signed and Sealed this

Nineteenth Day of October, 1999

Attest:

Q. TODD DICKINSON

*Attesting Officer*       *Acting Commissioner of Patents and Trademarks*

UNITED STATES PATENT AND TRADEMARK OFFICE
CERTIFICATE OF CORRECTION

PATENT NO. : 5,749,367

DATED : May 12, 1998

INVENTOR(S) : Lee Gamlyn, Siobhan O'Sullivan, Philip Needham and Tom Harris

It is certified that error appears in the above-identified patent and that said Letters Patent is hereby corrected as shown below:

Column 1, line 41, please delete "end" and insert --n--.

Column 2, line 38, please delete "detecting" and insert --detected--.

Column 3, line 63, please insert --a-- between "with" and "patient's".

Column 6, line 4, please delete "detecting" and insert --detected--.

Column 8, line 18, please insert --,-- between "50 Hz" and "typically".

Column 10, line 46, please delete "patent" and insert --pattern--.

Column 11, line 12, please delete "move" and insert --remove--.

Column 11, line 20, please delete "space" and insert --base--.

Column 11, line 50, please delete "amplifier" and insert --amplify--.

Column 11, line 62, please delete "IC6. The" and insert --IC6, the--.

Column 12, line 8, please insert --to-- between "connected" and "ground".

UNITED STATES PATENT AND TRADEMARK OFFICE
CERTIFICATE OF CORRECTION

PATENT NO. : 5,749,367

DATED : May 12, 1998

INVENTOR(S) : Lee Gamlyn, Siobhan O'Sullivan, Philip Needham and Tom Harris

It is certified that error appears in the above-identified patent and that said Letters Patent is hereby corrected as shown below:

Column 13, line 17, please delete "training" and insert --trailing--.

Column 13, line 42, please insert --digital-- between "serial" and "to".

Column 13, line 43, please insert --to-- between "connected" and "amplifier".

Column 14, line 9, please delete "measure" and insert --measured--.

Column 14, line 42, please delete "occur" and insert --occurs--.

Column 14, line 45, please delete "important" and insert --importance--.

Column 15, line 34, please delete "has" and insert --is--.

Column 15, line 48, please delete "once" and insert --or--.

Column 15, line 49, please insert --when-- between "S29" and "it".

Column 16, line 32, please delete "as well" and insert --unwell--.

Signed and Sealed this

Twenty-eighth Day of November, 2000

*Attest:*

Q. TODD DICKINSON

*Attesting Officer*   *Director of Patents and Trademarks*